(12) United States Patent
Jia et al.

(10) Patent No.: US 11,767,356 B1
(45) Date of Patent: Sep. 26, 2023

(54) CANINE PARVOVIRUS NANOBODY CPV-VHH-E3 AND APPLICATION THEREOF

(71) Applicant: Institute of Animal Sciences of CAAS, Beijing (CN)

(72) Inventors: Hong Jia, Beijing (CN); Hongfei Zhu, Beijing (CN); Qianqian Feng, Beijing (CN); Zhaoyang Wang, Beijing (CN); Weifeng Yuan, Beijing (CN); Zhongbao Pang, Beijing (CN)

(73) Assignee: INSTITUTE OF ANIMAL SCIENCES OF CAAS, Beijing (CN)

(*) Notice: Subject to any disclaimer, the term of this patent is extended or adjusted under 35 U.S.C. 154(b) by 0 days.

(21) Appl. No.: 17/983,727

(22) Filed: Nov. 9, 2022

(30) Foreign Application Priority Data

Nov. 12, 2021 (CN) .......................... 202111337192.1

(51) Int. Cl.
*C07K 16/08* (2006.01)
*C12N 15/79* (2006.01)
*A61K 39/23* (2006.01)
*A61K 39/00* (2006.01)

(52) U.S. Cl.
CPC ............ *C07K 16/084* (2013.01); *C12N 15/79* (2013.01); *A61K 39/23* (2013.01); *A61K 2039/552* (2013.01); *C07K 2317/569* (2013.01)

(58) Field of Classification Search
CPC C07K 16/084; C07K 2317/569; C12N 15/79; A61K 39/23; A61K 2039/552
See application file for complete search history.

(56) References Cited

U.S. PATENT DOCUMENTS

2017/0362310 A1  12/2017  Shoemaker

FOREIGN PATENT DOCUMENTS

| CN | 102219853 A | 10/2011 | |
|---|---|---|---|
| CN | 110964103 A | 4/2020 | |
| WO | WO 2020/099922 | * 5/2020 | ............. C07K 16/08 |

OTHER PUBLICATIONS

Genbank, "Immunoglobulin heavy chain variable region, partial [Vicugna pacos]", GenBank, Jul. 1, 2009.
Li Tongtong et al., "Preparation and Neutralization Activity of Anti-Canine Parvovirus", Journal of Chinese Biotechnology, Jan. 2, 2020, pp. 10-16, vol. 40, No. 4.

* cited by examiner

*Primary Examiner* — Nelson B Moseley, II
(74) *Attorney, Agent, or Firm* — WPAT, P.C

(57) ABSTRACT

Provided are a canine parvovirus (CPV) nanobody CPV-VHH-E3 and application thereof, belonging to the technical field of immunology. The nanobody CPV-VHH-E3 includes heavy chain variable region with amino acid sequence as shown in SEQ ID NO: 1, and a nucleotide sequence of a gene encoding the nanobody CPV-VHH-E3 is shown in SEQ ID NO: 2. The present application constructs a nanobody immune library for CPV by phage-display technology, and obtains specific anti-CPV nanobody CPV-VHH-E3 by screening, which is verified to specifically bind CPV through experiments, and is applicable to develop a nanobody preparation for clinical diagnosis and treatment of CPV, providing a certain theoretical support for the application of nanobodies in the field of veterinary biological products.

4 Claims, 16 Drawing Sheets

Specification includes a Sequence Listing.

FIG. 3

SEQUENCE LISTING

```
Sequence total quantity: 10
SEQ ID NO: 1                 moltype = AA   length = 139
FEATURE                      Location/Qualifiers
source                       1..139
                             mol_type = protein
                             organism = synthetic construct
SEQUENCE: 1
QLQLVESGGG SVQPGGSLRL SCAASGFTLD FYRVGWFRQA PGKERQGVAC IGSAGDRTFY   60
VDSVKGRFTI SKDNTKNTVY LQMNSLKPED TAVYYCAAVL SPRITSVQAM CTHHGEGFDY  120
WGQGTQVTVS SEPKTPKPQ                                               139

SEQ ID NO: 2                 moltype = DNA  length = 417
FEATURE                      Location/Qualifiers
source                       1..417
                             mol_type = other DNA
                             organism = synthetic construct
SEQUENCE: 2
cagttgcagc tcgtggagtc gggtggaggc tcggtgcaac ctgggggtc tctgagactc    60
tcctgtgcag cctctggatt cactttggat ttttatcgcg taggctggtt ccgccaggcc  120
ccagggaagg agcgtcaggg ggtcgcatgt attggtagtg ctggtgatag gaccttctat  180
gtggactccg tgaagggccg attcaccatc tccaaagaca acaccaagaa cacggtgtat  240
ctgcaaatga acagcctgaa acctgaggac acagccgttt attactgtgc agcagttctt  300
agtcctcgga ttactagtgt tcaggctatg tgtacccatc atggcgaagg gtttgactac  360
tggggccagg gacccaggt caccgtctcc tcagaaccca agacaccaaa accacaa      417

SEQ ID NO: 3                 moltype = DNA  length = 23
FEATURE                      Location/Qualifiers
source                       1..23
                             mol_type = other DNA
                             organism = synthetic construct
SEQUENCE: 3
gtcctggctg ctcttctaca agg                                           23

SEQ ID NO: 4                 moltype = DNA  length = 23
FEATURE                      Location/Qualifiers
source                       1..23
                             mol_type = other DNA
                             organism = synthetic construct
SEQUENCE: 4
ggtacgtgct gttgaactgt tcc                                           23

SEQ ID NO: 5                 moltype = DNA  length = 52
FEATURE                      Location/Qualifiers
source                       1..52
                             mol_type = other DNA
                             organism = synthetic construct
SEQUENCE: 5
gccatgactt ataggccc aggcggccca gttgcagctc gtggagtcag ga             52

SEQ ID NO: 6                 moltype = DNA  length = 57
FEATURE                      Location/Qualifiers
source                       1..57
                             mol_type = other DNA
                             organism = synthetic construct
SEQUENCE: 6
gccatgactt ataggccg gcctggccgg ggtcttcgct gtggtgcgcc gaggaga        57

SEQ ID NO: 7                 moltype = DNA  length = 22
FEATURE                      Location/Qualifiers
source                       1..22
                             mol_type = other DNA
                             organism = synthetic construct
SEQUENCE: 7
aagacagcta tcgcgattgc ag                                            22

SEQ ID NO: 8                 moltype = DNA  length = 24
FEATURE                      Location/Qualifiers
source                       1..24
                             mol_type = other DNA
                             organism = synthetic construct
SEQUENCE: 8
gcccccttat tagcgtttgc catc                                          24

SEQ ID NO: 9                 moltype = DNA  length = 54
FEATURE                      Location/Qualifiers
source                       1..54
                             mol_type = other DNA
                             organism = synthetic construct
```

```
SEQUENCE: 9
ggtggtgtac atctcctaca tctacgcccc cgggcaggtg cagctggtgg agtc         54

SEQ ID NO: 10           moltype = DNA   length = 59
FEATURE                 Location/Qualifiers
source                  1..59
                        mol_type = other DNA
                        organism = synthetic construct
SEQUENCE: 10
atggtgatgg tggtgctcga gttagtggtg gtggtggtgg tgagaggaga cggtgacct    59
```

CANINE PARVOVIRUS NANOBODY CPV-VHH-E3 AND APPLICATION THEREOF

CROSS-REFERENCE TO RELATED APPLICATIONS

This application claims priority to Chinese Patent Application No. 202111337192.1, filed on Nov. 12, 2021, the contents of which are hereby incorporated by reference.

TECHNICAL FIELD

The present application relates to the field of immunology and, in particular, to a canine parvovirus nanobody CPV-VHH-E3 and application thereof.

STATEMENT REGARDING SEQUENCE LISTING

The sequence listing associated with this application is provided in text format in lieu of a paper copy and is hereby incorporated by reference into the specification. The name of the XML file containing the sequence listing is 22046TDFS-USP1-2022-12259-sequence. The XML file is 10,609 bytes; was created on Mar. 22, 2023; contains no new matter; and is being submitted electronically via EFS-Web

BACKGROUND

Canine parvovirus (CPV), belonging to the family Parvoviridae and the genus Parvovirus, is a kind of DNA virus with a very fast mutation speed close to that of some RNA viruses. One of the most widely recognized stains of CPV is CPV type 2 (CPV-2), an outbreak of which was reported in the United States in 1978, and since then CPV has swept the world at a very rapid pace, with CPV-2a, CPV-2b, and CPV-2c mutant strains appearing one after another. Compared with the original CPV-2, the new mutant strains are more pathogenic and transmissible, making canines more susceptible and the host range more extensive, with cats also becoming susceptible and developing the disease; in particular, the CPV-2c mutant strain is much more virulent, more pathogenic and causes fatalities faster, all of which makes CPV prevention and treatment more difficult.

Currently, vaccination is one of the most effective means for preventing and controlling CPV, especially if administered to puppies at the appropriate time. Among varies vaccinations, live attenuated vaccine derived mostly from an attenuated strain of CPV-2 is the most commonly used vaccine with excellent effectiveness, good immunogenicity and a rather long duration of immunity. However, there are cases of failed immunization due to weak cross-protection between heterologous viruses as the wild strains continue to mutate; also, live attenuated vaccines are associated with biosafety risks such as spreading and returning virulence; though being widely used and providing excellent immune protection, live attenuated vaccines are therefore not the best choice for CPV prevention, and will be phased out eventually along with the continuous development of vaccine technology.

Heavy-chain-only antibodies (HCAbs) are antibodies composed of heavy chains only and light chains missed naturally, found only in camelids and sharks; antigen binding sites of these HCAbs are formed by a single structural domain, known as the variable domain of heavy chain of heavy chain antibody (VHH), and the antibody formed by cloning this structure is the smallest naturally occurring antibody fragment, also known as nanobody (Nab). Recent years have witnessed an increasing research on the application of nanobodies in animal diseases. For example, Yang Li (2017) et al. constructed an enzyme-linked immuno sorbent assay (ELISA) method for quantitative detection of porcine circovirus type 2 (PCV2) using recombinant anti-PCV2 nanobodies as capture antibodies, where nanobodies are applied to effectively reduce cross-reactivity in the detection and an improved method for determining virus content in producing porcine circovirus vaccines is provided. Yang Yan (2021) et al. constructed a nanobody library against bovine viral diarrhea virus (BVDV) by phage-display technology and screened nanobody sequences that react well with BVDV-NS3 protein, which laid a certain foundation for the prevention and control of BVDV and the development of nanobody applications. In contrast, no available reports of nanobodies for preventing, controlling and treating CPV have been published.

SUMMARY

The present application provides a canine parvovirus (CPV) nanobody CPV-VHH-E3 and its application in view of the problems mentioned above, whereby a nanobody immune library of CPV is constructed by using phage-display technology, then a CPV-specific nanobody CPV-VHH-E3 is obtained through screening, which is proved to be specifically binding to CPV through experiments.

To achieve the above objectives, the present application provides the following schemes:

a CPV nanobody CPV-VHH-E3, including a variable domain of heavy chain with an amino acid sequence as shown in SEQ ID NO:1, where the SEQ ID NO:1 is as follows:

QLQLVESGGGSVQPGGSLRLSCAASGFTLDFYRVGWFRQAPGKERQGVAC

IGSAGDRTFYVDSVKGRFTISKDNTKNTVYLQMNSLKPEDTAVYYCAAVL

SPRITSVQAMCTHHGEGFDYWGQGTQVTVSSEPKTPKPQ.

The present application also provides a gene encoding the CPV nanobody CPV-VHH-E3, and the gene has a nucleotide sequence as shown in the following SEQ ID NO: 2:

CAGTTGCAGCTCGTGGAGTCGGGTGGAGGCTCGGTGCAACCTGGGGGGTC

TCTGAGACTCTCCTGTGCAGCCTCTGGATTCACTTTGGATTTTTATCGCG

TAGGCTGGTTCCGCCAGGCCCCAGGGAAGGAGCGTCAGGGGGTCGCATGT

ATTGGTAGTGCTGGTGATAGGACCTTCTATGTGGACTCCGTGAAGGGCCG

ATTCACCATCTCCAAAGACAACACCAAGAACACGGTGTATCTGCAAATGA

ACAGCCTGAAACCTGAGGACACAGCCGTTTATTACTGTGCAGCAGTTCTT

AGTCCTCGGATTACTAGTGTTCAGGCTATGTGTACCCATCATGGCGAAGG

GTTTGACTACTGGGGCCAGGGGACCCAGGTCACCGTCTCCTCAGAACCCA

AGACACCAAAACCACAA.

An expression vector including the gene encoding the CPV nanobody CPV-VHH-E3 is disclosed by the present application.

Optionally, the expression vector includes pcDNA3.1.

A host cell including the expression vector is disclosed by the present application.

Optionally, the host cell includes HEK293F cell.

The present application provides an application of the CPV nanobody CPV-VHH-E3 in preparing anti-CPV drugs or vaccines.

The present application also provides a composition against CPV, which includes the nanobody CPV-VHH-E3.

The present application discloses the following technical effects:

- according to the application, the CPV immune library of nanobody is successfully constructed by phage-display technology, with an initial library capacity of $2*10^6$ colony-forming unit per millilitre (CFU/mL) and good diversity; specific sequence of nanobody CPV-VHH-E3 is successfully selected after three rounds of specific panning, then a recombinant nanobody CPV-VHH-E3 is successfully expressed by gene recombination technology through mammalian cell expression system, and is identified to be specifically binding to CPV by enzyme-linked immuno sorbent assay (ELISA) and indirect immunofluorescence assay (IFA). Accordingly, the present application develops a novel nanobody preparation which can be used in the clinical diagnosis and treatment of CPV, and provide a certain theoretical basis for the application of nanobody in the field of veterinary biological products.

BRIEF DESCRIPTION OF THE DRAWINGS

For a clearer description of the technical solutions in the embodiments or prior art of the present application, the drawings to be used in the embodiments are briefly described below, and it is obvious that the drawings in the following description are only some embodiments of the present application, and that other drawings can be obtained from these drawings without creative work by a person of ordinary skill in the art.

Figure 3:
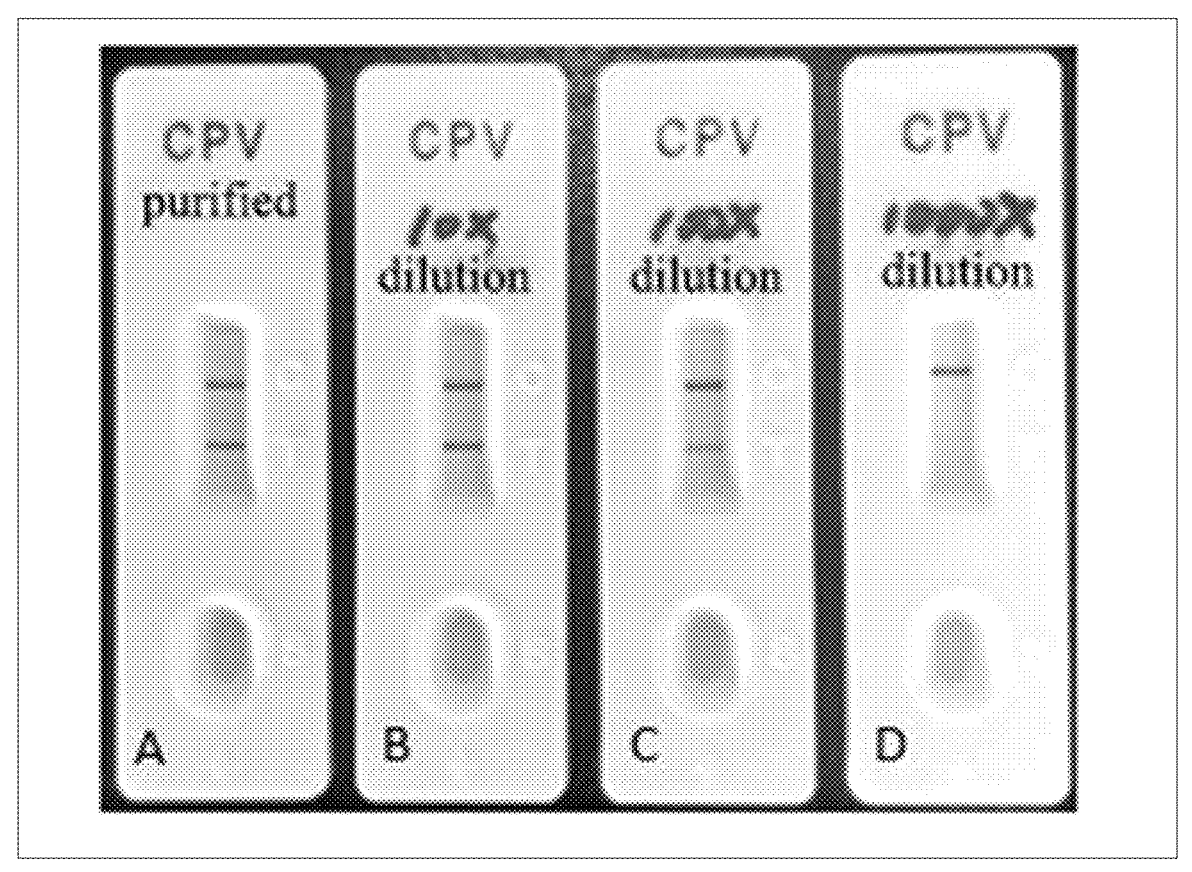

FIG. 3 shows detection results of purified virus, where A is purified CPV, B, C and D represents purified viruses of 10-fold dilution, 100-fold dilution and 1,000-fold dilution respectively.

DETAILED DESCRIPTION OF THE EMBODIMENTS

Figure 1:
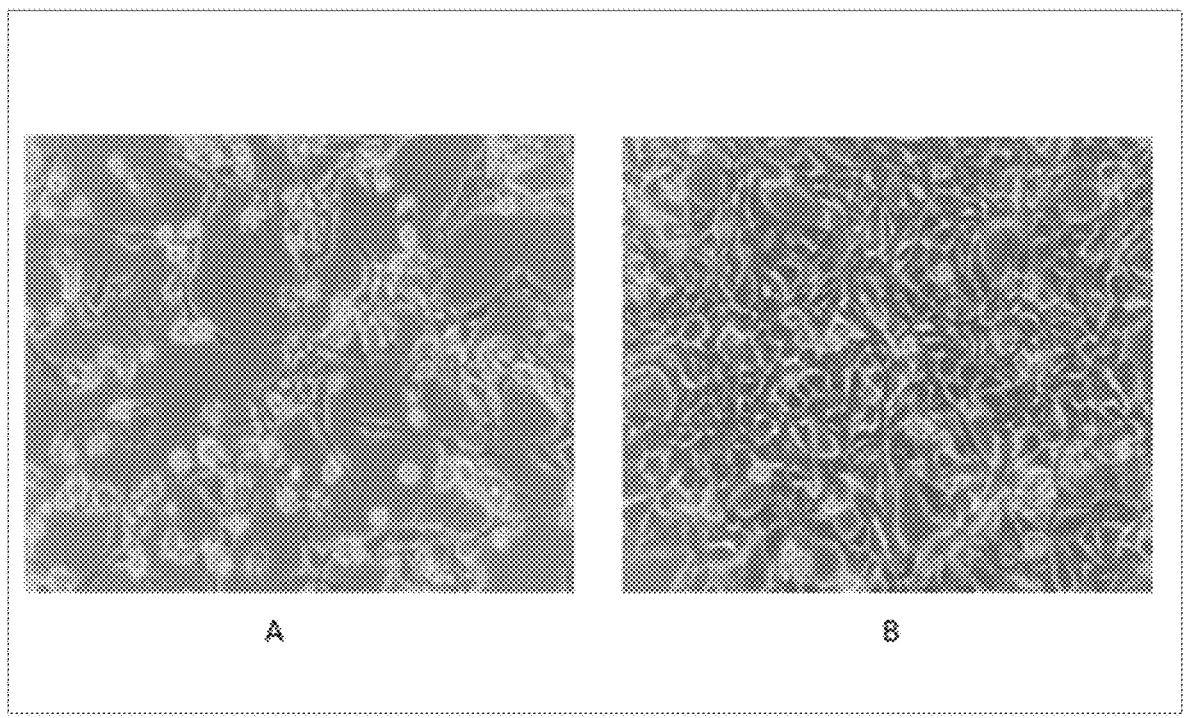
FIG. 1 illustrates cytopathic effect (CPE) of CPV-2c on crandell reese feline kidney (CRFK) cells, where A shows CPE after inoculating CPV-2c onto CRFK cells, and B shows normal CRFK cells.
Figure 2:
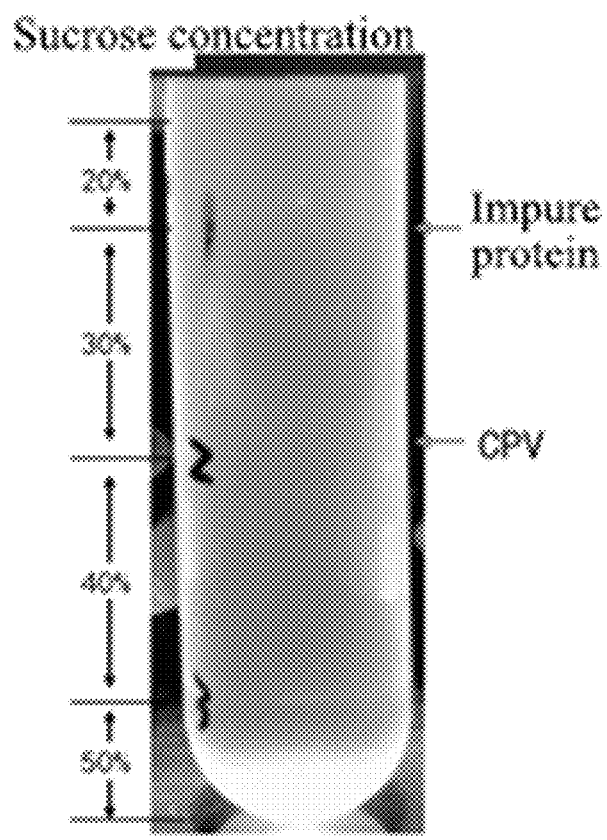
FIG. 2 shows CPV particles in sucrose density gradient in terms of position.
Figure 4:
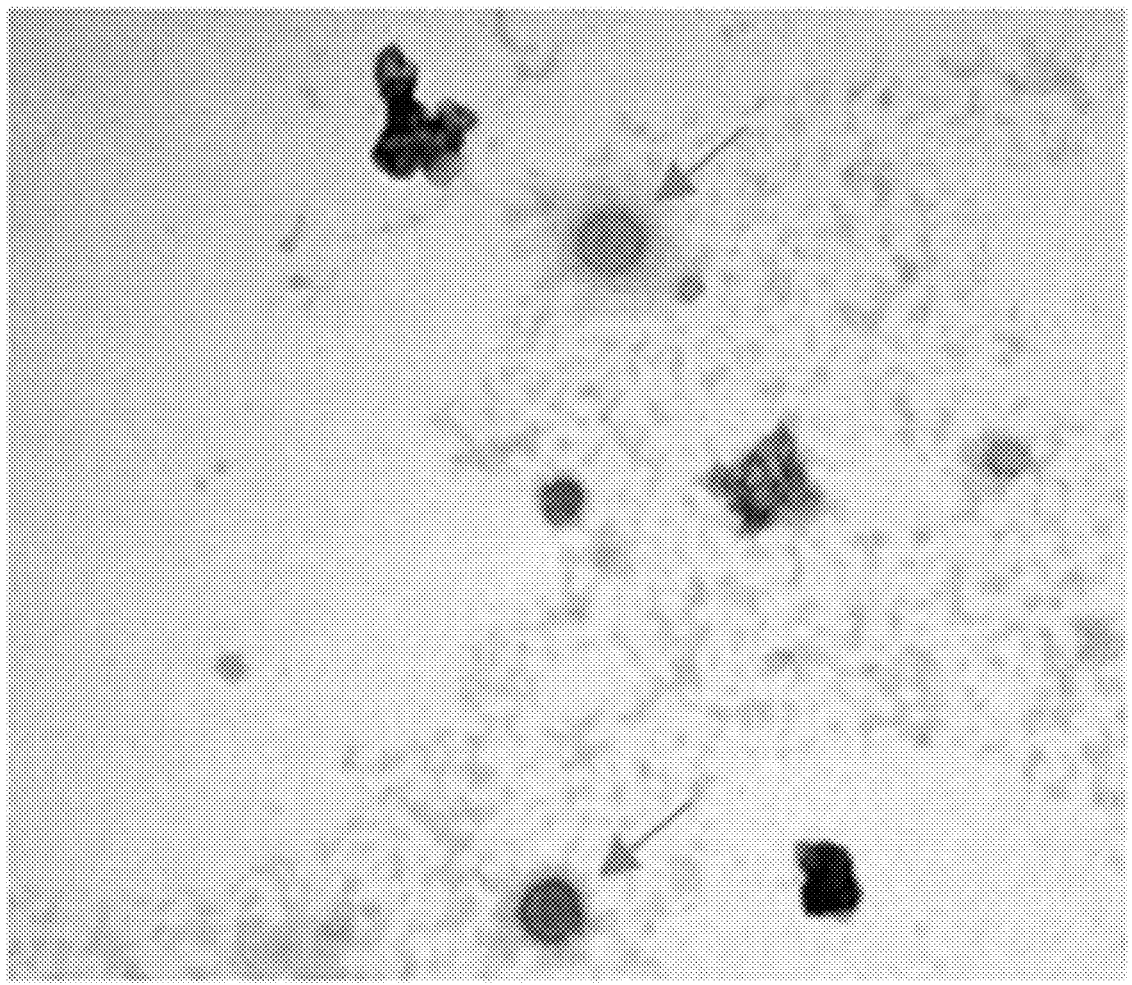
FIG. 4 is an electron microscope picture of CPV-2c.
Figure 5:
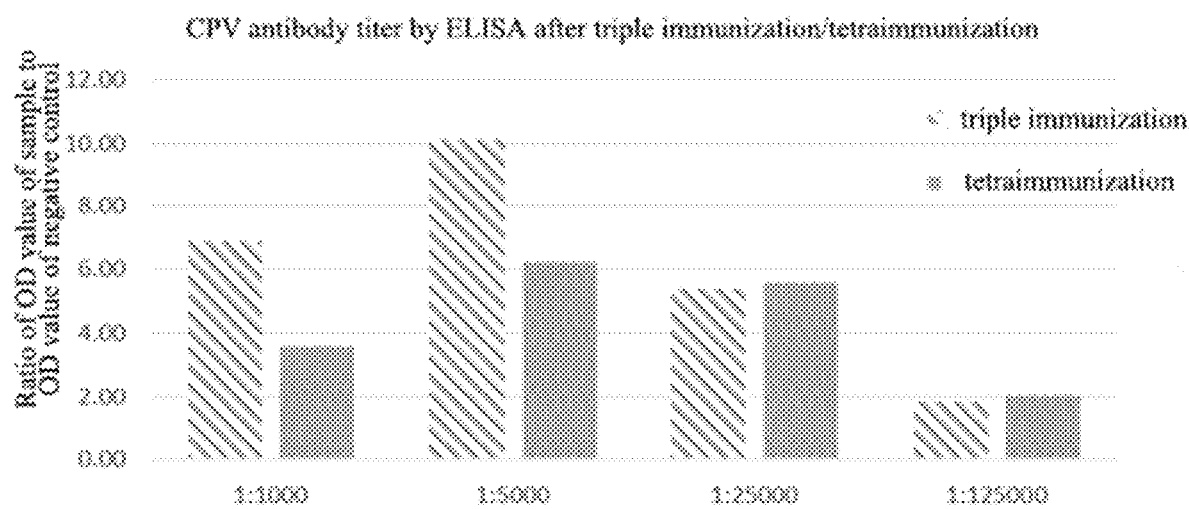
FIG. 5 illustrates titer of serum antibody detected by ELISA.
Figure 6:
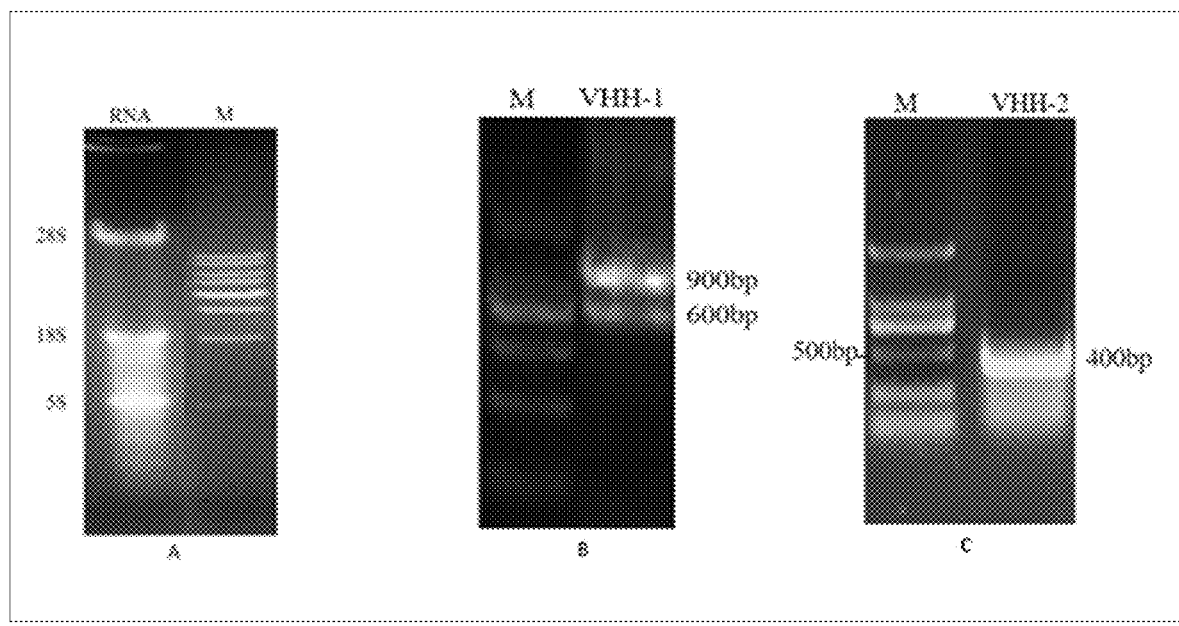
FIG. 6 shows PCR amplification results of VHH gene; where A: RNA, B: a first round of amplification products, C: a second amplification product (VHH).
Figure 7:
FIG. 7 shows colony numbers of an initial antibody library.

Various exemplary embodiments of the present application are now described in detail, and this detailed description should not be considered a limitation of the application, but should be understood as a rather detailed description of certain aspects, features and embodiments of the application.

It should be understood that the terms mentioned in the present application are only used to describe specific embodiments, and are not used to limit the present application. In addition, for the numerical range in the present application, it should be understood that each intermediate value between the upper limit and the lower limit of the range is also specifically disclosed. Every smaller range between any stated value or the intermediate value within the stated range and any other stated value or the intermediate value within the stated range is also included in the present application. The upper and lower limits of these smaller ranges can be independently included or excluded from the range.

Unless otherwise stated, all technical and scientific terms used herein have the same meanings commonly understood by those of ordinary skill in the field to which this application relates. Although the present application only describes preferred methods and materials, any methods and materials similar or equivalent to those described herein can be used in the practice or testing of the present application. All documents mentioned in this specification are incorporated by reference to disclose and describe the methods and/or materials related to the documents. In case of conflict with any incorporated documents, the contents of this specification shall prevail.

Without departing from the scope or spirit of the present application, it is obvious to those skilled in the art that many modifications and changes can be made to the specific embodiments of the present specification. Other embodiments obtained from the description of the present application will be obvious to the skilled person. The specification and embodiment of this application are exemplary only.

As used in this paper, the terms "including", "comprising", "having" and "containing" are all open terms, meaning including but not limited to.

Embodiment 1 Construction and Specific Screening of CPV Nanobody

1. Test Material
1.1 Viruses, cells, vectors and experimental animals
CPV-2c (TS02 strain F12), and crandell reese feline kidney (CRFK) (F86 generation) provided by Institute of Animal Science, Chinese Academy of Agricultural Sciences (CAAS); healthy alpaca (24-month-old, male) and pComb3x vector purchased from Abiocenter (Jiangsu) Biotechnology Co., Ltd.; TG1 competent cells purchased from Beijing Biomed Gene Technology Co., Ltd.; DH5a purchased from Nanjing Vazyme Biotech Co., Ltd.

1.2 Preparation of Main Reagent Solution

1) Luria-Bertani (LB) liquid medium: separately weighing 10 grams (g) of tryptone, 5 g of yeast extract and 10 g of sodium chloride, adding into about 800 milliliters (mL) of deionized water, stirring until they are completely dissolved and then fixing the volume to 1 liter (L), followed by sub-packing and autoclaving, then storing at room temperature for later use;

2) LB solid culture medium (Amp+): separately weighing 10 g of tryptone, 5 g of yeast extract and 15 g of agar powder, adding into about 800 mL of deionized water, heating and stirring until they are completely dissolved, then air-cooling to room temperature, fixing the volume to 1 L, autoclaving at 121 degree Celsius (° C.) for 20 minutes (min), adding 1 mL of ampicillin solution when the temperature drops to about 50° C., followed by mixing well and sub-packaging into disposable sterile culture dishes, and storing at 2-8° C. for later use after standing for solidification;

3) ampicillin solution (100 micrograms per milliliter (mg/mL) Amp): adding 5 g of ampicillin into about 40 mL of deionized water, fixing the volume to 50 mL after completely dissolving, filtering and sterilizing by a 0.22 micrometer (m) needle filter, then sub-packaging into 1.5 mL EP tubes and storing at −20° C.;

4) 20 mm Tris-HCl buffer with pH 8.0: adding 2.42 g of Tris powder into about 900 mL of deionized water, stirring to dissolve the powder and adjusting the pH to 8.0 with appropriate amount of hydrochloric acid, fixing the volume to 1 L at room temperature, filtering and sterilizing by a 0.22 m needle filter, then storing at room temperature for later use;

5) coating buffer (50 millimolars (mM) carbonate buffer with pH of 9.6): adding 1.59 g of sodium carbonate, 2.93 g of sodium bicarbonate into about 800 mL of deionized water, stirring for dissolving and adjusting the pH to 9.6, fixing the volume to 1 L;

6) 10×phosphate-buffered saline (PBS) buffer: dissolving 2 g of potassium dihydrogen phosphate, 29 g of disodium hydrogen phosphate dodecahydrate, 2 g of potassium chloride and 80 g of sodium chloride into about 800 mL of deionized water, followed by adjusting pH to 7.4 and fixing the volume to 1 L;

7) washing buffer (PBS with Tween 20, PBST): adding 100 mL of 10×PBS buffer and 0.5 mL of Tween-20 into deionized water and fixing volume to 1 L;

8) 20%/30%/40%/50% sucrose solution: separately weighing 6/9/12/15 g sucrose, respectively adding into 20 mM Tris-HCl buffer of about 20 mL, fixing the volume to 30 g with Tris-HCl buffer after completely dissolving, and filtering with 0.45 m needle filter for sterilization.

9) super optimal broth (SOC) medium: adding 20 g of tryptone, 5 g of yeast extract and 0.5 g of sodium chloride into about 900 mL of deionized water, followed by adding 10 mL of 250 mM potassium chloride, fixing the volume to 1 L after stirring and fully dissolving, and storing at room temperature for later use after autoclaving; 5 mL of sterile 2M magnesium chloride and 9 mL of sterile 40% glucose solution should be added before use.

2. Experimental Methods 2.1 Propagation and Purification of CPV

One tube of CRFK cryopreserved cells is recovered to dulbecco's modified eagle medium (DMEM) culture medium containing 5% fetal bovine serum (FBS), followed by culture in a 5% $CO_2$ incubator at 37° C. with passaging every 2-3 days, and expansion after cell status is stabilized; CPV-2c TS02 strain is inoculated synchronously at a ratio of 1% during cell passage, followed by culture at 37° C. in a 5% $CO_2$ incubator for 4-5 days; the cells are harvested when cytopathic effect (CPE) reaches about 80%, followed by freezing and thawing at −20° C. for 3 cycles then centrifuging at 8,000 revolutions per minute (rpm) for 5 min, collecting a supernatant; then the supernatant is concentrated 10 times by an ultrafiltration membrane bag with molecular weight cut-off of 10 Kilodalton (kD), followed by placing on 20% sucrose pad and subjecting to ultra-centrifugation at 30,000 rpm for 3 hours (h), with precipitate being resuspended with appropriate amount of 20 mM Tris-HCl buffer; after resuspension, the strain is placed on an upper layer of sucrose density gradient solution of 20%, 30%, 40% and 50%, followed by centrifugation at 35,000 rpm for 3 h, then virus bands in the area of 30%-40% sucrose density is sucked out with a syringe and diluted with a proper amount of Tris-HCl buffer, followed by ultra-centrifugation and precipitation to remove the sucrose in its suspension, with precipitate being resuspended with appropriate amount of Tris-HCl buffer to obtain purified virus suspension; then the purified virus suspension is identified by CPV antigen test strip and transmission electron microscope, and a protein concentration is measured by ultraviolet spectrophotometer as reference for later use.

2.2 Acquisition of Highly Immune Peripheral Blood 2.2.1 Vaccine Preparation and Immunization The purified virus is emulsified at a final concentration of 300 micrograms per liter (g/mL) with an equal volume of Freund's complete adjuvant/Freund's incomplete adjuvant to prepare vaccines; for a primary vaccination, one healthy male alpaca at 24 months of age is immunized with the vaccine formulated with Freund's complete adjuvant via multiple intramuscular injections (4 spots on each side of the spine and axilla, 0.2 mL per spot); booster immunizations are administered on the 14th, 28th and 42nd days after the primary vaccination respectively using vaccine formulated with Freund's incomplete adjuvant in a same manner and at a same dose as the primary vaccination.

2.2.2 Antibody Level Monitoring

Peripheral blood is collected from immunized alpaca on day 14 after a triple immunization and a tetraimmunization, respectively, with serum being isolated and tested in terms of CPV antibody titer by ELISA as follows:

(1) coating plate: diluting purified CPV to 5 μg/mL with coating buffer, followed by adding into 96 ELISA plate at 100 microliters per well (L/well), leaving overnight at 4° C., discarding the coating buffer, and washing with PBST for 5 times;

(2) sealing: adding 300 μL PBSM (PBS containing 5% skim milk powder) into each well and sealing at 37° C. for 2 h, discarding the PBSM and washing with PBST for 5 times, followed by spin-drying and storing at −20° C. for later use;

(3) dilution and incubation of sample serum to be tested: diluting the alpaca serum collected 14 days after the triple immunization and tetraimmunization by 1,000-fold, 5,-fold, 25,000-fold and 125,000-fold, respectively, followed by adding into coated ELISA plate, 100 L/well, 2 wells for each dilution; using alpaca serum not immunized with CPV as negative control, incubating at 37° C. for 1 h and then discarding serum that binds no antibody and washing with PBST for 5 times;
(4) second antibody incubation: adding 100 µL of Goat Anti-Alpaca IgG H & L (HRP) secondary antibody at 10,000-fold dilution to each well, followed by incubating for 1 h at 37° C.; then discarding the secondary antibody and washing 5 times with PBST;
(5) color development: adding 100 µL Tetramethylbenzidine (TMB) color development solution into each well, and incubating avoiding light for 15 min;
(6) termination: adding 50 µL 2M sulfuric acid solution to terminate the color development.
(7) result determination: measuring absorbance value of $OD_{450\ nm}$, considering the sample serum as positive if a ratio of an average of the absorbance values of sample serum and negative serum is larger than 2.1, and a highest dilution at which the absorbance value is positive is used as antibody titer of the serum.

2.2.3 Amplification of VHH Gene 2.2.3.1 Lymphocyte Isolation

About 30 mL of peripheral blood is collected from alpaca from jugular vein on the 14th day after the tetraimmunization, and sub-packed into anticoagulation tubes, which are slowly inverted several times to prevent blood clotting; lymphocytes are separated within 2 h according to instructions of lymphocyte isolation solution; the collected fresh blood is diluted with saline at a ratio of 1:1; 5 mL of lymphocyte separation solution is placed in a 10 mL horizontal centrifuge tube first, then 5 mL of diluted blood is slowly added above the lymphocyte separation solution, and the tube is centrifuged horizontally at 1,500 rpm for 20 min, followed by careful aspirating out white cloudy lymphocytes in a middle layer with a syringe; the lymphocytes isolated are diluted 5 times with saline and then carefully added again on top of an equal amount of lymphocyte separation solution and centrifuged horizontally at 1,500 rpm for 20 min; after repeating this procedure once, a final washout of lymphocytes is diluted and centrifuged at 1,000 rpm for 10 min, with precipitate being resuspended with an appropriate amount of saline; the isolated lymphocytes should be extracted as soon as possible, or stored frozen at −70° C. after adding with appropriate amount of Trizol.

2.2.3.2 RNA Extraction

RNA is extracted by Trizol method with specific operations as follows:
(1) placing 100 µL of isolated lymphocyte suspension in a centrifuge tube, adding with 1 mL of Trizol, mixing by repeated blowing and then leaving it at room temperature for 5-10 min;
(2) adding 0.2 mL of chloroform, shaking vigorously for 15 seconds (s) and then leaving it at room temperature for 5 min;
(3) centrifuging at 12,000 rpm for 15 min to allow visible stratification, aspirating an upper aqueous phase into a new centrifuge tube;
(4) adding with an equal volume of pre-cooled isopropanol, mixing well and leaving at room temperature for 10 min;
(5) centrifuging at 12,000 rpm for 15 min, discarding supernatant and rinsing precipitate with 1 mL of 75% ethanol containing no RNaes enzyme;
(6) centrifuging at 8,000 rpm for 10 min, discarding clear supernatant, and leaving the precipitate to dry at room temperature for 5-10 min; and
(7) adding 50 µL diethyl pyrocarbonate (DEPC) water to resuspend the precipitate with appropriate blowing, and accelerating dissolution by water bath at 56° C. for 5 min; taking a small amount of RNA solution to determine OD value and subject to gel electrophoresis detection, and freezing the remaining RNA solution at −80° C.

2.2.3.3 Reverse Transcription

RNA tested to be of acceptable quality is reverse transcribed according to an instructions of Takara's cDNA synthesis kit, with specific operation illustrated as follows:
1) preparing a reaction mixture in a PCR tube according to Table 1:

TABLE 1

| Reverse transcription system 1 | |
| --- | --- |
| Reagent | Volume (µL) |
| Oligo dT Primer | 1 |
| Random 6 mers | 1 |
| dNTP Mixture (10 mM each) | 1 |
| Total RNA | 5 |

2) reacting at 65° C. for 5 min and then quickly cooling in ice powder for 2 min;
3) adding the following components as shown in Table 2 into the above reaction mixture; and

TABLE 2

| RNA reverse transcription system 1 | |
| --- | --- |
| Reagent | Volume (µL) |
| Above reaction mixture | 10 |
| 5 × PrimeScript II Buffer | 4 |
| RNase Inhibitor (40 U/µL) | 0.5 |
| PrimeScript II RTase (200 U/µL) | 1 |
| RNase Free dH$_2$O | 4.5 |

4) standing all the above reaction mixtures at 30° C. for 10 min, reacting at 42° C. for 50 min, reacting at 95° C. for 5 min and then storing at −20° C.

2.2.3.4 PCR Amplification of VHH Gene

Two rounds of Nested PCR primers are designed according to a method of Yanli Yang et al. (Yang et al., 2019) to remove interference of VH genes in alpaca, while Sfi I cleavage sites are introduced in a second round of PCR primers with the following primer sequences:

first round of PCR primers:

```
VHH F1 (SEQ ID NO: 3):
5'-GTCCTGGCTGCTCTTCTACAAGG-3';

VHH R1 (SEQ ID NO: 4):
5'-GGTACGTGCTGTTGAACTGTTCC-3';
``` second round PCR primers:

```
Sfi I-VHH F2 (SEQ ID NO: 5):
5'-GCCATGACTTATATAGGCCCAGGCGGCCCAGTTGCAGCTCGTGGAGT
CAGGA-3' (underlined part is Sfi I cleavage site);

Sfi I-VHH R2 (SEQ ID NO: 6):
5'-GCCATGACTTATATAGGCCGGCCTGGCCGGGGTCTTCGCTGTGGTGC
```

-continued

GCCGAGGAGA-3' (underlined part is Sfi I cleavage site);

cDNA obtained through reverse transcription of 2.2.3.3 is used as template to amplify VHH gene fragment using the first round of PCR primers, with PCR reaction system as shown in Tables 2-5 and amplification procedure as shown in Table 4. PCR products are identified by 1.0% nucleic acid gel electrophoresis, and are used as templates after confirming a successful amplification of a target band of about 400 bp in size to carry out the second round of PCR amplification; as referring to Tables 3 and 4, the second round of PCR amplification adopts PCR reaction system and amplification procedure same as those of the first round; and final amplification product is identified by gel electrophoresis with target fragment gel being recovered.

TABLE 3

PCR amplification system

| Reagent/sample | Volume (μL) |
| --- | --- |
| template | 5 |
| Upstream primer | 2 |
| Downstream primer | 2 |
| 2 × Phanta Max MasterMix | 25 |
| ddH$_2$O | 16 |
| Total volume | 50 |

TABLE 4

PCR amplification procedure

| Process | Reaction temperature | Reaction duration |
| --- | --- | --- |
| predenaturation | 95° C. | 5 min |
| denaturation | 95° C. | 10 s |
| annealing | 56° C. | 15 s |
| extending | 72° C. | 30 s |
| re-extension | 72° C. | 10 min |
| preservation | 4° C. | ∞ |

2.2.4 Construction of M13 Phage Antibody Library
2.2.4.1 Vector Construction

Target fragment recovered from the second round PCR in 2.2.3.4 and pComb3x vector are digested with Sfi I enzyme with a digestion reaction system as shown in Table 5, including: adding each component into the PCR tube, centrifuging briefly to precipitate the components into a bottom of the tube, and reacting at 37° C. overnight.

TABLE 5 enzyme digestion reaction system

| Reaction component | Volume |
| --- | --- |
| Sfi I | 1 μL |
| 10 × CutSmart Buffer | 5 μL |
| Target fragment/vector | 1 μg |
| ddH2O | Up to 50 μL |
| Total volume | 50 μL |

The digested product is identified by nucleic acid electrophoresis gel and the target fragment is recovered. A ligation system is adjusted according to the concentration of recovered nucleic acid, the VHH gene fragment is ligated with pComb3x vector using T4 DNA ligase under reaction of 37° C. for 30 min as shown in Table 6.

TABLE 6

T4 DNA ligase ligation system

| Reaction component | Volume |
| --- | --- |
| T4 DNA Ligase | 1 μL |
| 10 × T4 DNA Ligase Buffer | 1 μL |
| Target fragment and vector recovered after enzyme digestion | molar ratio of fragment to vector of about 1:3 |
| ddH$_2$O | Up to 10 μL |
| Total volume | 10 μL |

2.2.4.2 Electrotransformation

Ligation product is introduced into TG1 competent cells by electrotransformation, with specific steps as follows:
(1) thawing one tube of electrotransformed TG1 receptor cells on ice, adding 10 μL of ligation product after complete thawing of the receptor cells, and leaving it on ice for 10 min, keeping the whole operation on ice as much as possible;
(2) gently moving the above receptor cells into a prechilled electrotransformation cup with 1 electric shock at 1,800 volts (V), immediately adding 1 mL of SOC culture solution and gently transferring to a 2 mL EP tube;
(3) incubating at 37° C. with shaking of 200 rpm for 1 h, coating all on LB (Amp+) solid plates, and incubating overnight at 37° C. upside down;
(4) collecting all colonies growing on the plate into 5 mL LB medium and adding 5 mL LB medium containing 40% glycerol, which is the initial antibody library of anti-CPV nanobodies, and storing them at −80° C. after sub-packaging.

2.2.4.3 Identification of Initial Antibody Library
1) Determination of storage capacity: 10 μL of the initial antibody library bacterial solution is diluted 1,000 times with LB medium, and 200 μL of the diluted bacterial solution is spread on a solid LB (Amp+) medium plate and incubated overnight at 37° C. in inverted position; the next day, the number of colonies on the plate is counted and the library capacity of the initial library is calculated according to the following formula, and the library capacity meets the screening requirement by reaching $10^5$ to $10^6$, and the volume is calculated with unit of L;

Library capacity (CFU/mL)=(number of colonies/
volume of coated bacterial solution)×dilution
times×(1,000/volume of original library
samples).

2) Detection of positive rate: 48 randomly selected single colonies from the above plates are added to 500 μL LB (Amp+) medium and incubated for 4 h at 37° C. with 200 rpm; using this as a template, PCR amplification is performed with amplification primers Sfi I-VHH F2 and Sfi I-VHH R2 of VHH gene, and the amplification system and conditions are the same as those illustrated in Tables 2-5 and Tables 2-6; PCR products after detection by 1.5% gel electrophoresis are used for the calculation of the positive rate.

(3) Analysis of antibody library diversity: 20 bacterial solutions that tested positive by PCR as described above are then selected and sent to sequencing company for sequencing, and the sequencing results are analyzed and phylogenetic trees are drawn using DNA-MAN and MEGA softwares to analyze the antibody library in terms of diversity.

2.2.5 Panning and Enrichment of CPV-Specific Recombinant Phage

2.2.5.1 Expansion and Rescue of VHH Antibody Library 1) adding 100 µL of the initial library bacterial solution into 100 mL of LB (Amp+) medium and incubating for 4-6 h at 37° C. with shaking, so that the $OD_{600}$ value of the solution reaches 0.6-0.8;
2) adding auxiliary phage M13K07 in an addition amount calculated according to a multiplicity of infection (MOI) of 20:1, standing at 37° C. for 30 min, then incubating with shaking at 180 rpm and 37° C. for 30 min;
3) centrifuging the above bacterial solution at 5,000 rpm for 10 min under room temperature and discarding supernatant;
4) resuspendeding the bacterial solution with 200 mL of LB (Amp+, Kana+) medium at 30° C. with 200 rpm shaking overnight;
5) centrifuging the above culture solution at 4° C. and 8,000 rpm for 20 min, collecting supernatant into a clean and sterile glass triangular flask, to which 1/5 volume of 5×PEG/NaCl solution is slowly added, then standing for 5 h at 4° C.;
6) centrifuging at 4° C., 8,000 rpm for 30 min, discarding supernatant, resuspending precipitate with 2 mL PBS, mixing well, centrifuging at 8,000 rpm for 2 min, discarding the precipitate, adding 40% glycerol to the supernatant at a ratio of 1:1, subpackaging it into sterile EP tubes, and storing at −20° C., then obtaining the CPV-specific recombinant phage library.

2.2.5.2 Selection and enrichment of CPV-specific recombinant phage

The ELISA Plate is Coated with Purified CPV as the Target Antigen, and the Phage library rescued in 2.2.5.1 is panned for a total of 3 rounds, with each round gradually decreasing the amount of coating antigen to screen out CPV-specific recombinant phages with higher affinity, the specific operations are as follows:

(1) antigen coating plate: diluting the purified CPV with coating buffer to 100 µg/mL (first round panning), 10 µg/mL (second round panning) and 1 µg/mL (third round panning) respectively, and respectively adding into 96-well ELISA plate, 100 µL/well, culturing overnight at 4° C., discarding the coating buffer and washing with PBST for 5 times;
(2) sealing: adding 300 µL PBSM (PBS containing 5% skimmed milk powder) per well, sealing for 2 h at 37° C., discarding the PBSM, washing 5 times with PBST, spin-drying and then storing at −20° C. for later use;
(3) recombinant phage library dilution: taking 1 mL of the rescued recombinant phage library, adding 9 mL of PBSM for dilution, mixing well and leaving it at 37° C. for 1 h;
(4) binding: adding the diluted recombinant phage library to the coated ELISA plate, 100 L/well, reacting by shaking at 37° C. and 80 rpm for 30 min, and then leaving at 37° C. for 2 h;
(5) washing: discarding fluids in the wells, washing 5 times with PBST, then 5 times with PBS, discarding washing solution, and spin-drying; washing times should be increased accordingly for the second and third rounds of panning to further reduce non-specific binding;
(6) initial infestation: adding 100 µL of TG1 bacterial solution cultured to logarithmic growth phase to each well, incubating for 20 min at 37° C. and collecting the bacterial solution;
(7) elution: adding 200 µL of eluent (200 mM glycine, pH 2.2) per well and placing it on a microshaker for 10 min with light shaking;
(8) neutralization: aspirating out eluate from the wells and quickly adding with 1M Tris buffer (pH 9.0) to adjust the pH to 7.4 to restore the infection ability of the phage;
(9) re-infection and amplification: adding the above eluate to 5 mL of TG1 bacterial solution cultured to logarithmic growth stage, then mixing with that of the initial infection, and leaving it at 37° C. for 2 h; adding 100 mL LB (Amp+) medium, culturing with shaking at 37° C. for 4-6 h to make the OD600 of bacterial solution reach 0.6-0.8; and
(10) rescue: adding auxiliary phage M13K07 and following step 2) to 6) of 2.2.5.1 for rescuing.

The supernatant after precipitation and resuspension is the recombinant phage library amplification solution obtained from the first round of panning, and the rest after partial preservation for the next round of panning, the second and third round of panning steps are the same as the first round, see steps (3) to (10).

2.2.6 Phage Monoclonal Detection

2.2.6.1 Preparation of Monoclone

Taking 100 µL of a mixture of the second infection at the third round of panning (see 2.2.5.2 step 9), coating it on a solid LB (Amp+) medium plate after fold dilution and incubating it overnight at 37° C. in an inverted position, preparing phage monoclone according to the following steps:

(1) adding LB (Amp+) liquid medium in 96-well deep-well plate, 800 µL/well, selecting 96 single colonies randomly from the medium plate, adding them to the deep-well plate, and incubating at 37° C. and 200 rpm overnight, using this as the master plate;
(2) taking another 96-well deep-well plate, add 800 µL LB (Amp+) liquid medium to each well, inoculating with 100 µL of bacterial solution from each corresponding well of the master plate, and incubating at 37° C. and 200 rpm for 2 h, and taking this as a detecting plate; adding 50% glycerol at 600 L/well to the master plate after inoculation, and freezing at −20° C.;
(3) adding the auxiliary phage M13K07 with MOI of 20:1 to the incubated detecting plate, leaving it in an incubator at 37° C. for 30 min, and then incubating it by shaking at 37° C. and 200 rpm for 30 min;
(4) placing the detecting plate in a rotor of enzyme plate of centrifuge, centrifuging at 4,000 rpm for 20 min at room temperature, discarding the supernatant, resuspending the bacteria by adding 800 µL LB (Amp+, Kana+) medium to each well, and then incubating at 37° C. with shaking at 200 rpm overnight; and
(5) centrifuging the detecting plate again at 4° C. and 4,000 rpm for 40 min, aspirating out the supernatant of each well and adding into a new 96-well deep-well plate correspondingly, which is the monoclone of the phage, and storing at 4° C. for later use.

2.2.6.2 ELISA Detection of CPV-Specific Phage

The above monoclone of the phage is used as primary antibody for ELISA detection as follows:

(1) plate coating: diluting purified CPV to 1 µg/mL with coating buffer, adding into 96-well ELISA plate at 100 µL/well, overnight at 4° C., discarding coating buffer, and washing with PBST for 5 times;
(2) sealing: adding 300 µL PBSM (PBS containing 5% skimmed milk powder) to each well, sealing for 2 h at 37° C., discarding the sealing solution, washing 5 times with PBST, shaking dry and storing at −20° C. for later use;

(3) adding 90 μL PBSM per well, adding the phage monoclone obtained in 2.2.6.1 to the corresponding wells of the ELISA plate, setting up a negative control plate without antigen in parallel, all at 10 μL/well, incubating for 2 h at 37° C. and discarding the fluids in the wells, washing 5 times with PBST;

(4) incubation of secondary antibody: adding 100 μL of HRP-labeled mouse anti-M13 antibody at 1,000-fold dilution to each well, incubating for 1 h at 37° C. and then discarding the secondary antibody and washing 5 times with PBST;

(5) color development: adding 100 μL TMB color development solution into each well, and incubating in the dark for 15 min;

(6) termination: adding 50 μL 2M sulfuric acid solution to terminate the color development; and (7) result determination: measuring absorbance value of $OD_{450\ nm}$, considering the sample serum as positive if the ratio of an average of the absorbance values of sample serum and negative serum is larger than 2.1.

2.2.6.3 Positive Monoclone Sequencing

Based on the ELISA results, the monoclones with high positive values are selected and PCR amplification is performed with universal primer of pComb3x vector (see Table 7), and the amplification system and conditions are the same as Table 3 and Table 4. PCR products are sent to the company for sequencing, and the sequencing results are analyzed by DNAMAN software.

TABLE 7

Universal primers of pComb3x vector

| Primer | Primer sequence (5'→3') |
|---|---|
| pComb3x-F (SEQ ID NO: 7) | AAGACAGCTATCGCGATTGCAG |
| pComb3x-R (SEQ ID NO: 8) | GCCCCCTTATTAGCGTTTGCCATC |

2.3 Results and Analysis 2.3.1 Propagation and Purification of CPV

After inoculation of CRFK cells with TS02 strain CPV-2c virus, cytopathic lesions are clearly observed after 72 hours of incubation at 37° C.; the inoculated cells are harvested approximately 96 hours after inoculation when the cytopathic lesions reach 80%-90% (FIG. 1), and the cells are freeze-thawed three times at −20° C. to obtain a supernatant; the supernatant of the cell culture is subjected to ultrafiltration, ultracentrifugation and sucrose density gradient separation to obtain purified CPV; as shown in FIG. 2, 2 major protein bands are observed in the concentrated cell culture supernatant after sucrose density gradient centrifugation, which are collected separately and detected by CPV antigen detection test strips to determine that CPV is mainly concentrated between 30% and 40% of the sucrose gradient; and the protein concentration of the purified virus suspension is approximately 1.2 mg/mL as determined by an ultraviolet (UV) spectrophotometer.

The purified CPV is diluted 10-fold, 100-fold and 1,000-fold and detected by CPV antigen detection test strips, respectively, with a loading volume of 100 μL. The results show that the antigen detection line is still visible after the purified virus is diluted 1,000-fold (FIG. 3), and the virus antigen detection line is obvious after 10 to 100-fold dilution, indicating a high degree of enrichment of purified CPV particles; as shown in FIG. 4, the CPV particles (about 20-30 nm in diameter) can be found quickly with less heteroproteins other than the viral particles; consequently, the purified CPV can be used as an antigen for the construction of CPV-specific phage library.

2.3.2 Antibody Level after Immunization

Peripheral blood of immunized alpacas is collected 14 days after the triple immunization and tetraimmunization, respectively, and the serum is separated and the antibody level of CPV is determined by indirect ELISA; the serum is diluted to 1,000, 5,000, 25,000 and 125,000 times as primary antibody and added to the enzyme plate coated with CPV, while the negative serum of non-immunized alpacas is used as negative control and Goat Anti-Alpaca IgG H&L (HRP) is used as secondary antibody; the ratio of the $OD_{450}$ nm value of the final sample to be tested to the $OD_{450}$ nm value of the negative serum >2.1 is judged to be positive at that dilution; among the positive test results, the highest dilution is considered as the CPV antibody titer of the serum. Results of $OD_{450\ nm}$ values are shown in Table 8, and the antibody titer results are shown in FIG. 5, from which it can be seen that the serum titer can reach 1:25000 after both the triple immunization and tetraimmunization, and the antibody at this level can be used for the preparation of immune antibody libraries.

TABLE 8

ELISA experimental data

| | Serum dilution multiple and average $OD_{450nm}$ | | | |
|---|---|---|---|---|
| Group | 1:1,000 | 1:5,000 | 1:25,000 | 1:1,250,000 |
| Triple immunization serum | 1.0910 | 0.7170 | 0.2590 | 0.0800 |
| Negative serum | 0.1580 | 0.0710 | 0.0480 | 0.0440 |
| Tetraimmunization serum | 1.318 | 0.995 | 0.463 | 0.135 |
| Negative serum | 0.371 | 0.16 | 0.083 | 0.067 |

2.3.3 PCR Amplification Results of VHH Gene

About 30 mL of peripheral blood is collected from alpacas on the 14th day after tetrahymenorrhea, the lymphocytes are isolated according to the instructions of the lymphocyte isolation kit, and RNA is extracted from the lymphocytes by Trizol method, see FIG. 6 for the results of RNA extraction; there are obvious 28S and 18S bands at 5K and 2K in the extracted RNA samples (FIG. 6A), indicating that the RNA quality is good and can be used for the amplification of VHH sequences; after reverse transcription of the RNA, two bands at 600 bp and 900 bp are observed in the amplified product with the first round of PCR primers (FIG. 6 B), and the product after the second round of amplification using this as a template has a clear band at 400 bp (FIG. 6C), which is consistent with the expected size of the VHH fragment.

2.3.4 Identification Results of Initial Antibody Library 2.3.4.1 Capacity of the Initial Antibody Library The target fragment of VHH amplified in the second round is recovered and ligated with pComb3x vector by enzymatic digestion, and the initial library of VHH is obtained by electrotransforming TG1 receptor cells; 10 μL of the initial antibody library solution is taken and diluted 1,000 times, then 200 μL of the diluted solution is coated onto an LB (Amp+) plate and incubated upside down overnight at 37° C.; the number of colonies on the plate is counted the next day to be about 4,000 (FIG. 7), and the library capacity of the initial antibody library is calculated to be about $2.0*10^6$ CFU/mL, which is in line with the expected library capacity of the immune library and can be used for specific phage panning.

Figure 8:
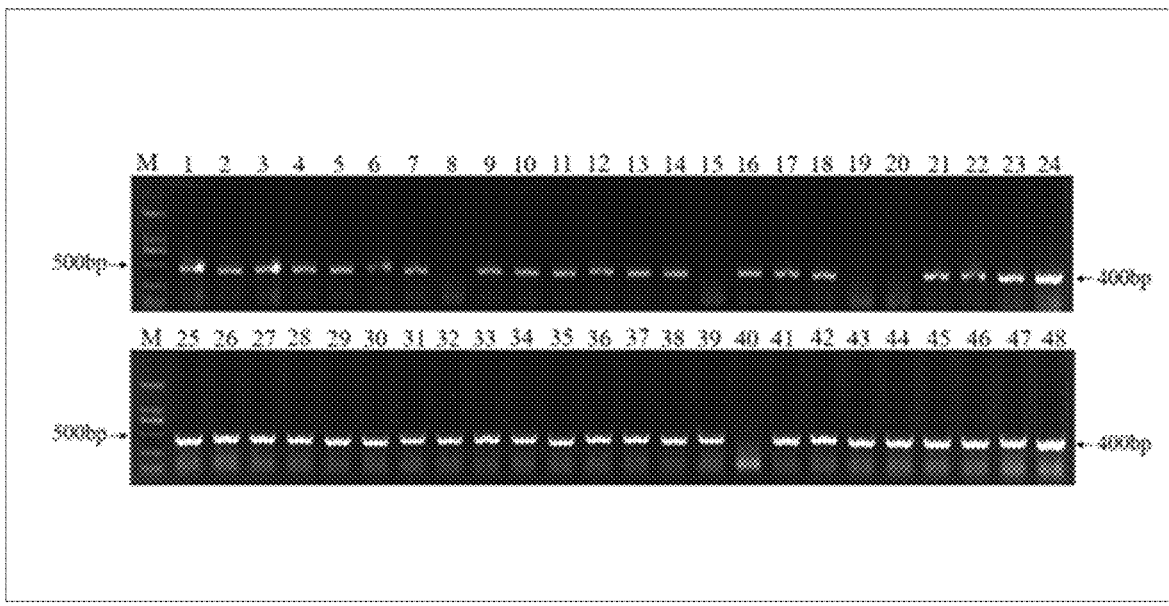
FIG. 8 shows polymerase chain reaction (PCR) results of bacterial solution, where M stands for Maker, and 1-48 refer to single colony samples.

2.3.4.2 Positive Rate of Initial Antibody Library 48 single colonies are randomly picked out from the colony plates of the above library capacity determination, added to 500 µL LB (Amp+) medium, then incubated for 4 h at 37° C. with shaking at 200 rpm; they are used as templates to amplify the VHH gene with specific primers, and the gel electrophoresis results of the PCR products are shown in FIG. 8, including 43 positive samples and 5 negative samples, with a recombination rate of about 89.6%.

2.3.4.3 Diversity of Initial Antibody Library 20 positive monoclones are analyzed by DNAMAN software for amino acid sequence comparison, resulting in 78.9% homology of the 20 VHH genes and a large difference in CDR3 region, indicating a good diversity of genes in the heavy chain variable region in the initial library. By plotting the genetic evolutionary tree of the sequences by MEGA software, it is found that the homology of the sequences is more different from each other, which further indicates that the initial library has good diversity and can be used for the screening of specific phage.

2.3.5 Phage Monoclonal Detection and Sequencing Results

The phage infected by the third round of panning is subjected to multiple dilution with LB medium, and then coated onto solid LB (Amp+) plate medium after dilution and incubated upside down at 37° C. overnight; 96 monoclones are randomly picked out from the plate on the next day and multiplied as primary antibody for ELISA detection, and the results show that 59 of the 96 monoclones are CPV-specific positive clones, accounting for 61.5%, and the highest P/N value can be up to 22, indicating that the high affinity recombinant phage that can bind specifically to CPV is effectively enriched after three rounds of panning.

2.3.6 Monoclone Sequencing

Figure 9:
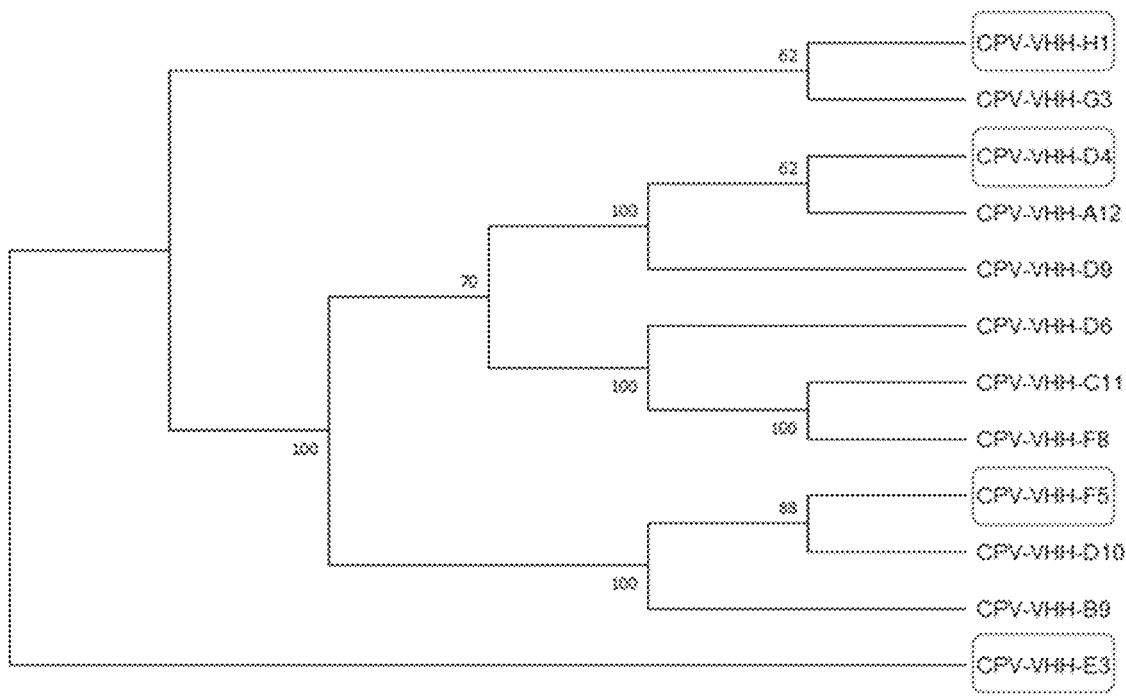
FIG. 9 shows a phylogenetic tree analysis of sequences.

The first 12 monoclonel strains with high P/N values in ELISA screening are sent to gene company for sequencing, where each sequence is compared and analyzed, and the phylogenetic tree is drawn (FIG. 9), from which four sequences with the greatest differences are selected for VHH expression and identification, namely CPV-VHH-H1, CPV-VHH-D4, CPV-VHH-F5 and CPV-VHH-E3.

Embodiment 2 Expression and Identification of Nanobodies Against CPV

1. Experimental Materials 1.1 Cells, Vectors and Virus Species

HEK293F cells, CRFK cells, pcDNA3.1 vector and CPV-2c strain (TS02 strain, F15 generation, 106.5 $TCID_{50}$/1 mL) provided by Institute of Animal Science, CAAS. DH5a competent cells were purchased from TransGen Biotech Co., Ltd.

1.2 Solution Preparation

1) Polyethylenimine (PEI) solution (1 mg/mL): adding 100 mg PEI powder to 90 mL ultrapure water, slowly adding HCl while stirring to adjust pH to less than 2.0 and then continue stirring for 3-4 h until the powder is completely dissolved; after complete dissolution, slowly adding NaOH (10 mol/L) to adjust pH to 7.0, and then fixing the volume to 1 L with a measuring cylinder; then filtering and sterilizing by 0.22 m needle filter and sub-packing into 1.5 mL centrifuge tube at 1 mL/tube, storing at −80° C. for later use; after thawing, it can be stored at 4° C. for 30 days, and repeated freeze-thawing should be avoided.

2) Protein Purification Solution

Binding buffer: 20 mM Tris, 500 mM NaCl, 20 mM imidazole, adjusting the pH to 8.0 with hydrochloric acid;

washing buffer: 20 mM Tris, 500 mM NaCl, 60 mM imidazole, adjusting pH to 8.0 with hydrochloric acid;

elution buffer: 20 mM Tris, 500 mM NaCl, 500 mM imidazole, and adjusting the pH to 8.0 with hydrochloric acid.

3) Protein gel staining solution: adding 1 g of coomassie brilliant blue G250 into 1 L of a solution containing 25% isopropyl alcohol and 10% glacial acetic acid, and stirring until it is completely dissolved;

4) Decolorizing solution of protein gel: adding 100 mL of acetic acid and 50 mL of absolute ethanol into 850 mL of deionized water, and mixing well; and 5) 5×SDS-PAGE electrophoresis buffer: adding 15.1 g of Tris, 94 g of glycine, 5 g of SDS into deionized water, and fixing volume to 1 L; diluting 5 times with deionized water before use.

2. Experimental Methods 2.1 Construction of VHH Recombinant Expression Vector 2.1.1 Primer Design Sequences of 4 phage strains selected by panning are used to design and synthesize universal primers with Xma I and Xho I cleavage sites, while 6×His tag sequence is added at the N-terminal end of the antibody sequence, the primer sequences are as follows.

VHH-F (SEQ ID NO: 9):
5'-GGTGGTGTACATCTCCTACATCTACGCC<u>CCCGGG</u>CAGGTGCAGCTGG

TGGAGTC-3' (the underlined part is the cleavage site of Xma I);

VHH-R (SEQ ID NO: 10):
5'-ATGGTGATGGTGGTG<u>CTCGAG</u>TTAGTGGTGGTGGTGGTGGTGAGAGG

AGACGGTGACCT-3' (underlined part is the cleavage site of Xho I).

2.1.2 Amplification of the Target Gene

The plasmid DNAs extracted from the four strains are used as templates for PCR amplification, with reaction systems and reaction procedures as shown in Table 9 and Table 10, and the amplified products are detected by 1% agarose gel electrophoresis.

TABLE 9

| PCR amplification system | |
|---|---|
| Reagent/sample | Volume (µL) |
| template | 2 |
| VHH-F and VHH-R | 2 for each |
| 2 × Phanta Max MasterMix | 25 |
| ddH$_2$O | 19 |
| Total volume | 50 |

TABLE 10

| PCR amplification procedure | | |
|---|---|---|
| Process | Reaction Temperature | Reaction duration |
| predenaturation | 95° C. | 5 min |
| denaturation | 95° C. | 30 s |
| annealing | 56° C. | 30 |
| extending | 72° C. | 1 min |

TABLE 10-continued

PCR amplification procedure

| Process | Reaction Temperature | Reaction duration |
| --- | --- | --- |
| re-extension | 72° C. | 5 min |
| preservation | 4° C. | ∞ |

2.1.3 Enzyme Digestion, Ligation and Transformation

The target fragment DNA is recovered according to the instructions of the agarose gel recovery kit and the nucleic acid concentration is measured by an UV spectrophotometer. The recovered target fragment is double digested with the pcDNA3.1 vector using Xma I and Xho I enzymes, respectively; the enzyme digestion reaction system is shown in Table 11, and the components are mixed and briefly centrifuged down to the bottom of the tube and placed at 37° C. for digestion overnight.

TABLE 11

Double enzyme digestion reaction system

| Reaction component | Volume |
| --- | --- |
| Xma I and Xho I | 1 μL each |
| 10 × CutSmart Buffer | 5 μL |
| VHH target fragment/pcDNA3.1 vector | 1 μg |
| ddH$_2$O | Up to 50 μL |
| Total volume | 50 μL |

After the enzyme digestion reaction, the target fragment is recovered by nucleic acid electrophoresis, and the VHH gene fragment is ligated with pcDNA3.1 vector using T4 DNA ligase, with ligation reaction system as shown in Table 12; all components are added into 1.5 mL EP tubes and centrifuged briefly down to the bottom of the tubes, and ligated at 37° C. for 30 min.

TABLE 12

T4 DNA ligase ligation system

| Reaction component | volume |
| --- | --- |
| T4 DNA Ligase | 1 μL |
| 10 T4 DNA Ligase Buffer | 1 μL |
| Target fragments and vectors recovered after enzyme digestion | The molar ratio of fragment to carrier is about 1:3. |
| ddH$_2$O | Up to 10 μL |
| Total volume | 10 μL |

The ligation products are transformed into DH5α receptor cells, an on the next ay of transformation, 12 monoclones are picked out from the plates into EP tubes containing 500 μL of LB (Amp+) medium and incubated at 200 rpm for 4 h; the positive rate of transformation is identified with universal primers of the vector, and three positive strains from each group are selected and sent to the company for sequencing; based on the sequencing results, strains with correct sequence ligation and no mutation are used to extract plasmid DNA of recombinant expression vector for VHH gene expression.

2.2 Transient Expression of VHH in HEK293F

HEK293F cells are recovered and cultured at 37° C. with 5% CO$_2$ and shaking at 140 rpm, passaging once every 2-3 days, where the density should reach 3.0*10$^6$ cells/mL at the time of passaging, and the initial density is 0.3-0.5*10$^6$ cells/mL after passaging; cells should be passaged at least 2 times after resuscitation, so that the cell status is stable and the survival rate is greater than 98% before using for transfection experiments.

HEK293F cells are transfected as follows:

(1) HEK293F cells that have been cultured for 2-3 days are counted the day before transfection and the cell density is adjusted to 1.5*10$^6$ cells/mL, where the addition of fresh medium should be greater than 50% of the final volume, and this ratio can be achieved by centrifuging the cells to replace the fresh medium;

(2) on the day of transfection, cells are counted and the cell concentration is adjusted to 2.0*10$^6$ cells/mL with fresh medium and sub-packed into 6-well cell culture plate at 2.5 mL/well;

(3) plasmid DNA in appropriate amounts as well as PEI solution are added to 300 μL Opti-MEM medium respectively, so that the final concentration of DNA at the time of transfection is 1 μg/mL and the final concentration of PEI is 5 μg/mL; the diluted DNA is filtered through a 0.22 μm filter to remove bacteria, and mixed well with the diluted PEI solution, followed by standing for 20 min at room temperature and then slowly added into the prepared wells; and (4) the pcDNA3.1-EGFP vector is meanwhile used as a control plasmid and transfected under the same conditions.

After transfection, the cells are cultured at 37° C. with 5% CO$_2$ and shaking at 140 rpm for 7 days, during which fresh medium is added in appropriate amounts according to the cell status; after the culture, the cell culture solution is collected and centrifuged at 8,000 rpm for 5 min to remove cells and cell debris, and the cell culture supernatant is harvested with a small amount of which being subjected to SDS-PAGE to detect the expression of the target protein, and the remaining samples are stored at −20° C.

2.3 Purification of VHH 2.3.1 Affinity Purification of Ni-Magnetic Beads

The target protein with 6×His tag is purified by Ni-magnetic bead affinity purification as follows:

(1) adding 2-fold volume of binding buffer into the supernatant of cell culture solution, mixing, adding 1% volume of Ni-magnetic beads, oscillating and adsorbing at 80 rpm for 2 h, placing on a magnetic rack to separate the magnetic beads, and discarding the supernatant;

(2) washing the magnetic beads with 5 times of the loading volume of the washing buffer for 3 times to wash away impure proteins as much as possible;

(3) adding elution buffer in 1/20 times the volume of the original cell supernatant, eluting for 10-30 min at room temperature, and collecting the eluate.

2.3.2 Exchange, Concentration and Detection of Purified Protein

The purified antibody protein is exchanged for liquid using a ultrafiltration tube with a 3 kD cut-off molecular weight, and the elution buffer containing imidazole is replaced with 20 mM Tris-HCl (pH 8.0) while concentrating.

2.3.3 Identification of VHH

The purified antibody proteins are identified by SDS-PAGE, indirect ELISA, IFA and virus neutralization test (VN) against CPV.

2.3.4 SDS-PAGE Detection

The purified antibody proteins are examined for concentration and purity by SDS-PAGE; 30 μL of purified protein solution and 30 μL of cell culture supernatant are added respectively with 10 µL of 4× loading buffer, and then briefly centrifuged and boiled in boiling water for 10 min; the prepared SDS-PAGE gel plate is loaded into a vertical electrophoresis tank with appropriate amount of electrophoresis buffer; the prepared sample and protein Marker are added into the wells of the gel plate respectively, with 10 µL/well; electrodes of the electrophoresis tank are connected correctly and electrophoresis is carried out at a constant pressure of 180 V; the electrophoresis is stopped when the bromophenol blue migrates to the bottom of the gel plate; then the gel is taken out and placed in an appropriate amount of protein gel staining solution, and the staining solution is slightly shaken for about 30 min, then the staining solution is rinsed off with water and replaced with an appropriate amount of protein gel decolorizing solution, and the gel is shaken off until the background is clear and transparent.

2.3.5 Indirect ELISA Detection

The indirect ELISA method is as follows:

1) antigen coating: diluting the purified CPV to 10 µg/mL with coating buffer, adding the diluted CPV antigen solution to the ELISA plate, 100 µL/well, and leaving it overnight at 4° C.; discarding the coating buffer and washing with PBST for 5 times;
2) sealing: adding 300 µL of PBSM (PBS containing 5% skimmed milk powder) to each well, sealing for 2 h at 37° C., discarding the sealing solution, washing 5 times with PBST, and spin-drying;
3) primary antibody incubation: diluting the purified nanobodies with 5% PBSTM (dilutions of 1:10, 1:100, 1:1,000 and 1:10,000, respectively), adding the diluted antibodies to ELISA plates at 100 uL/well, making 3 parallel groups for each dilution and setting up a negative control at the same time. incubating for 1 h at 37° C., washing 5 times with PBST and spin-drying;
4) enzyme-labeled secondary antibody incubation: diluting anti-His-HRP antibody 1: 3,000 with 5% PBSTM, 100 uL/well, incubating for 1 h at 37° C. and then discarding the secondary antibody, washing 5 times with PBST and spin-drying;
5) TMB color development: adding 50 µL TMB color development solution into each well, and incubating avoiding light for 15 min;
6) termination: adding 50 µL 2M sulfuric acid solution to terminate the color development;
7) result determination: measuring $OD_{450\ nm}$ value by microplate reader.

2.3.6 IFA Detection

The IFA detection operates as follows:

(1) cell plating and inoculation: taking one bottle of CRFK cells (T75) with full monolayer of CRFK cells, taking ¼ cell suspension after digestion and adding into 20 mL of DMEM medium containing 5% FBS, mixing well and plating 48-well cell plate, 200 L/well; diluting the CPV strain 20 times, adding it into the above cells with 100 L/well, and sealing the plate, followed by incubation at 37° C. with 5% $CO_2$ for 72 h;
(2) fixation: discarding the cell culture supernatant, slowly adding pre-cooled anhydrous ethanol at 100 µL/well, and incubating overnight at 4° C.;
(3) sealing: discarding fixing solution, washing 3 times with PBST, 600 µL/well for 2 min each time, then using PBSTM containing 5% skimmed milk powder as sealing solution to seal the cells at 400 L/well for 1 h at 37° C., washing 3 times with PBST;
(4) primary antibody incubation: diluting the purified nanobodies 10 times with 5% PBSTM, adding the diluted nanobodies to ELISA plates, 100 µL/well, and setting up CPV mouse multiple antibody positive control (1:10 dilution) and negative control at the same time, incubating at 37° C. for 1 h and washing with PBST for 5 times;
(5) secondary antibody incubation: diluting anti-His-FITC antibody 1:1,000 times with 5% PBSTM, adding 100 µL to each well, adding 1:1,000 times diluted anti-mouse-FITC as secondary antibody to the CPV mouse multiple antibody positive control wells, incubating for 1 h at 37° C. and protected from light, washing 5 times and adding 200 µL PBST to each well to keep it moist, and storing at 4° C. and protected from light; and
(6) observing experimental results under fluorescent microscope.

2.3.7 Antibody Detection (VN) of Virus Neutralizing Test

CPV neutralizing test operates as follows:

(1) nanobody dilution: dilute the purified recombinant expressed nanobodies 5 times with DMEM, respectively, and adding them to the first row of 96-well cell plate after sterilization by 0.22 m needle filter, 100 µL per well, and continuing 2-fold (100 µL+100 µL) serial dilution to 1:640, making 3 replicates for each dilution, and setting up both virus control and uninfected normal cells control wells;
(2) virus dilution: diluting CPV-2c cytotoxin (F15 generation, 106.5 $TCID_{50}$/mL) 30,000-fold with DMEM (approximately 100 $TCID_{50}$ per 100 µL) and adding it to the cell wells that have been diluted with antibody, 100 µL/well; further diluting the diluted virus solution above in a 10-fold series to $10^{-1}$, $10^{-2}$ and $10^{-3}$, containing 10, 1 and 0.1 $TCID_{50}$, respectively, and adding to the cell wells without antibodies as a virus regression experiment, 100 µL per well, 5 wells per dilution;
(3) neutralizing: shaking and mixing the above cell plates for 10 s, and then incubating them at 37° C. for 1 h, mixing every half hour;
(4) adding cells: adding digested cell suspension (containing 15% FBS) to the neutralized cell wells at 60 µL per well; and
(5) cultivation and observation: placing the cell plates in an incubator containing 5% $CO_2$ at 37° C. for 7 days to observe the cell lesions.

3. Results and Analysis 3.1 Construction of VHH Recombinant Expression Vector

Figure 10:
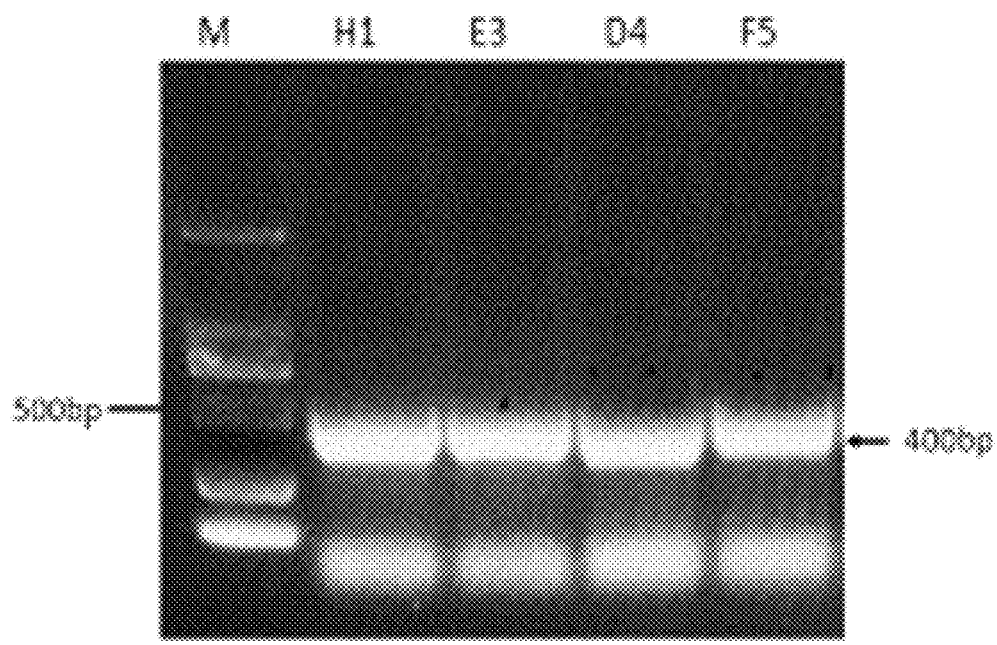
FIG. 10 shows a PCR amplification product of VHH gene.
Figure 11:
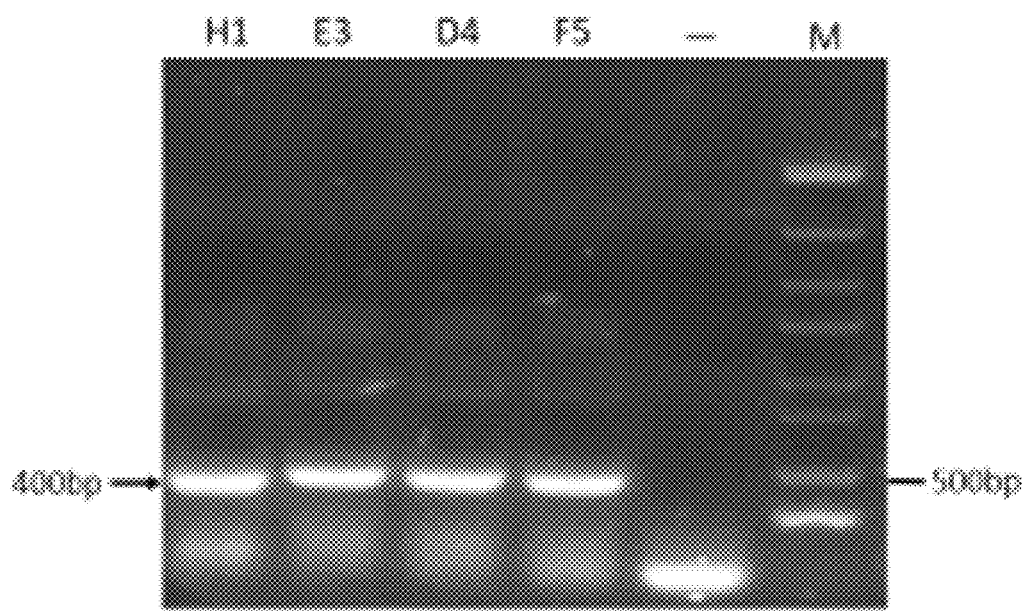
FIG. 11 is an enzyme-digested product of VHH gene.

Specific primers are designed according to the sequences of four selected phage strains CPV-VHH-H1, CPV-VHH-E3, CPV-VHH-D4 and CPV-VHH-F5, and four VHH fragments of about 400 bp in size are amplified (FIG. 10), which meet the expected results; gel recovered fragments and the lab-constructed pcDNA3.1 vector (with bee venom signal peptide and Xma I digestion site already added) are subjected to double digestion with Xma I and Xho I enzymes, respectively, and the digested products are shown in FIG. 11; gel of about 400 bp in size is cut and the target fragments are recovered according to the instructions of the gel recovery kit.

Figure 12:
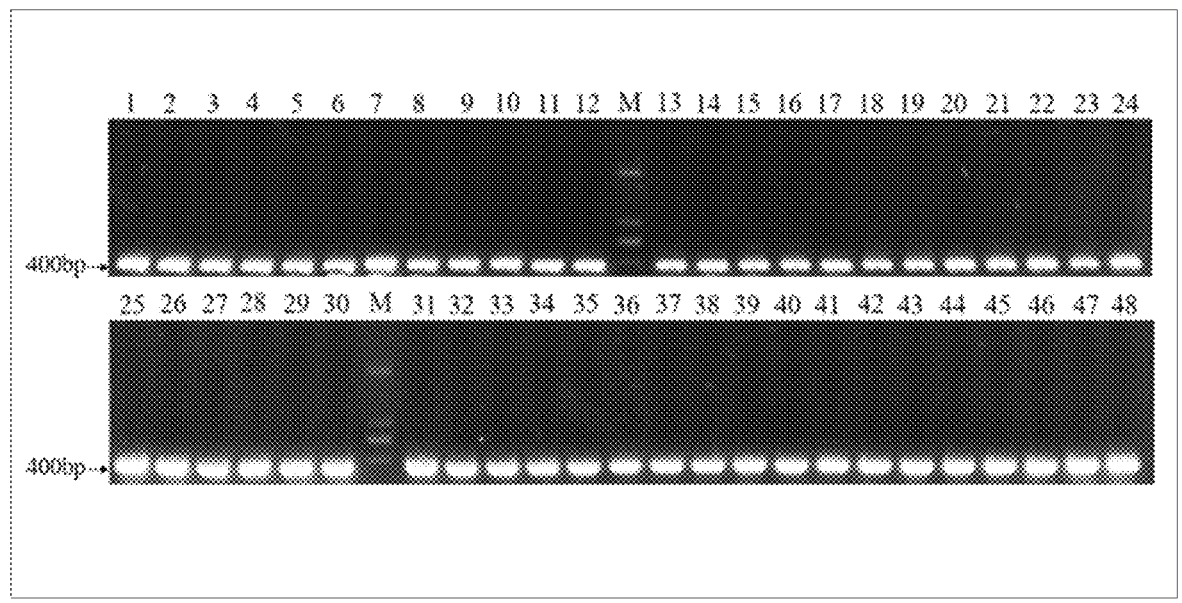
FIG. 12 shows PCR identification of recombinant expression vector pcDNA3.1-VHH, where M: 2K DNA Maker; 1-12: pcDNA3.1-VHH-H1; 13-24: pcDNA3.1-VHH-E3; 25-36: pcDNA3.1-VHH-D4; 37-48: pcDNA3.1-VHH-F5.

The fragment and vector are ligated with T4 ligase and are used to transform DH5a receptor cells; 12 single colonies are randomly selected from each group on the next day, and the target fragment is amplified with specific primers after amplification, the PCR product is detected by gel electrophoresis and all single colonies are positive, which means the transformation positivity rate is 100% (FIG. 12).

Three positive clones from each group are randomly selected and sent to sequencing company for sequencing. DNAMAN is used to compare the sequencing results, which shows that the sequences of at least two of the three clones in each group are correctly ligated and free of mutations, proving that the recombinant expression vector pcDNA3.1-VHH of the four nanobodies is successfully constructed and can be used for mammalian cell expression of recombinant nanobodies.

3.2 Transient Expression of VHH

Figure 13:
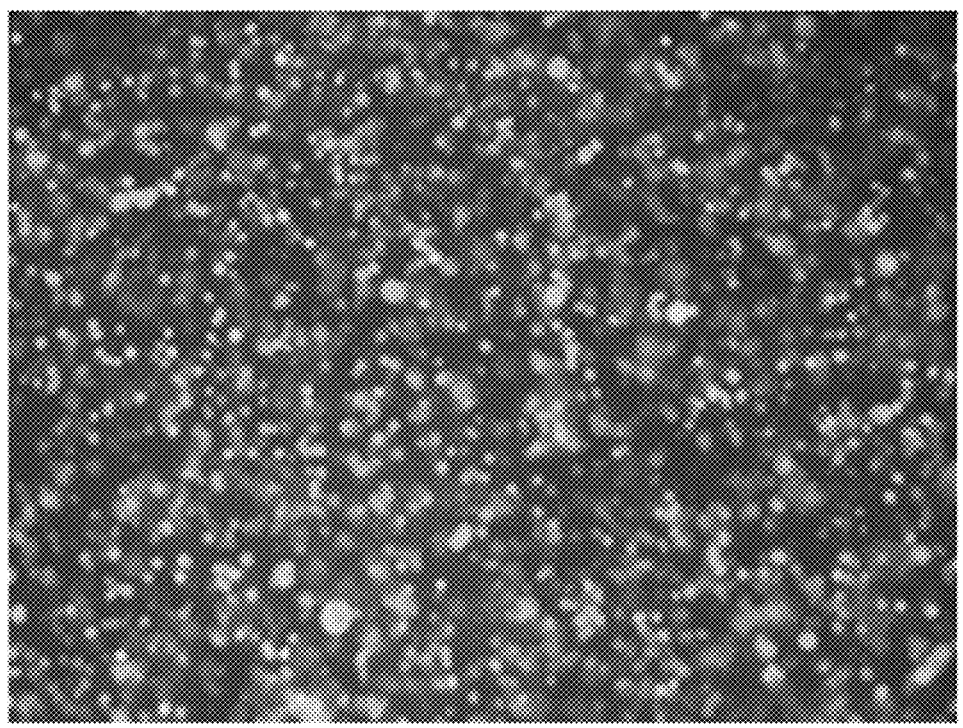
FIG. 13 is a fluorescence diagram 24 hours after transfection of a control vector pcDNA3.1-EGFP.
Figure 14:
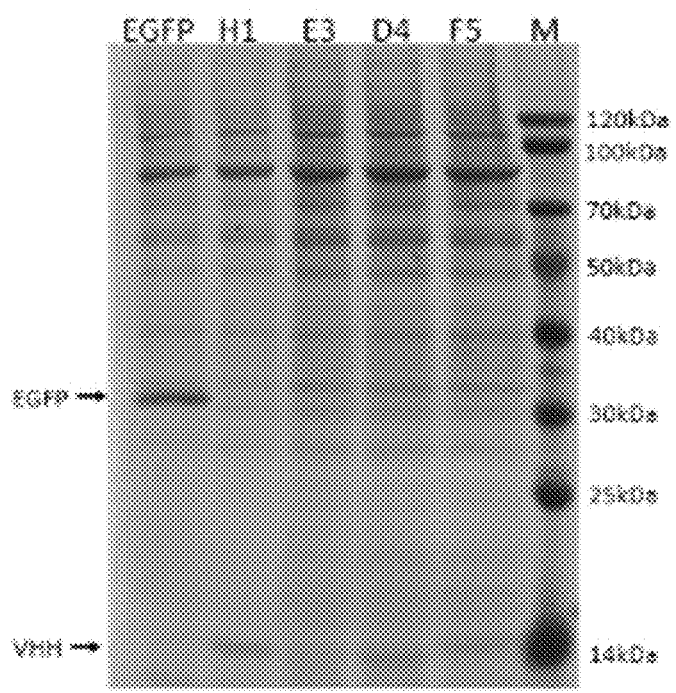
FIG. 14 shows sodium dodecyl sulfate polyacrylamide gel electrophoresis (SDS-PAGE) result of cell culture supernatant.

See FIG. 13 for the transfection effect of the control plasmid observed by fluorescence microscopy on the second day after transfection, the number of cells with/without fluorescence is counted, and the transfection efficiency is calculated to be about 50%; the cell supernatant is harvested on the 7th day after transfection and detected by SDS-PAGE, which shows the target protein bands with a size of about 14 kD and a lower expression, and an obvious EGFP control protein band with a size of about 30 kD is visible (FIG. 14).

3.3 Purification of VHH

Figure 15:
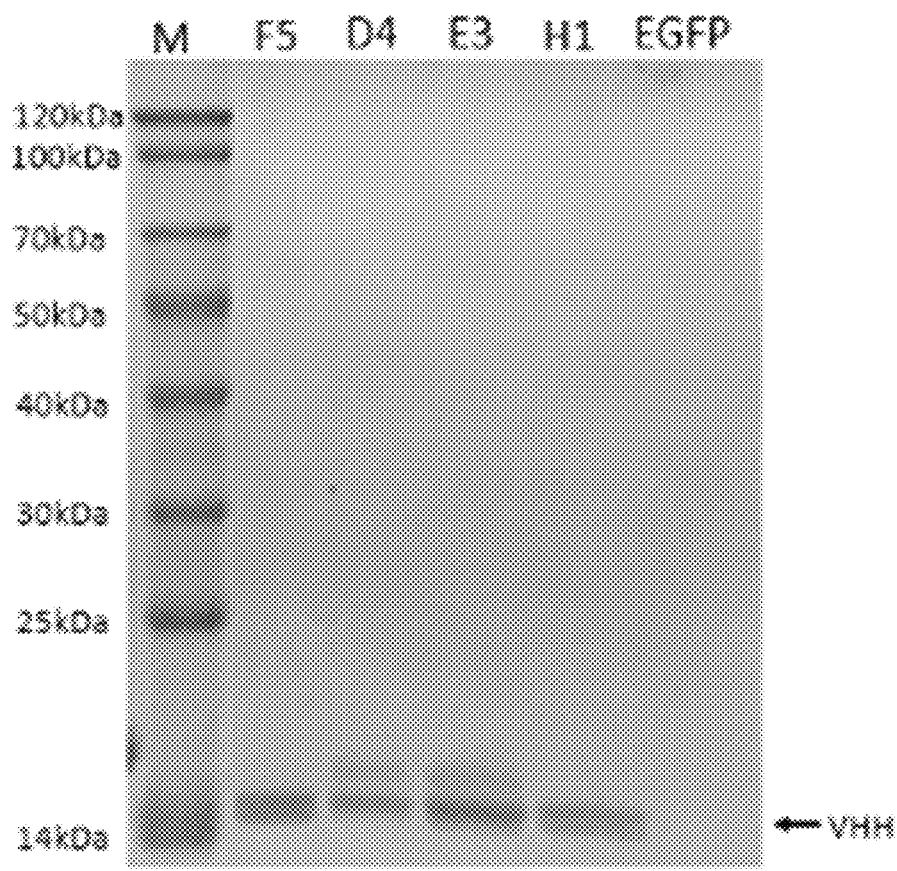
FIG. 15 is the SDS-PAGE result of purified VHH.

All four groups of recombinant VHH cell culture supernatants and control cell culture supernatants expressing EGFP are subjected to affinity purification by Ni-magnetic beads, and the purified samples show obvious VHH target bands (FIG. 15) with a size of about 15 kDa and a protein purity of >90%, while the control protein is not enriched by Ni-magnetic beads, which is in accordance with the expected results.

The above experiments prove that a total of four nanobodies, CPV-VHH-H1, CPV-VHH-E3, CPV-VHH-D4 and CPV-VHH-F5, have been successfully expressed, and the recombinant nanobody proteins can be effectively enriched by the tag protein 6×His.

3.4 Identification of VHH 3.4.1 Results of Indirect ELISA

The four expressed nanobodies are identified by indirect ELISA in terms of specificity; when the ratio of the $OD_{450\ nm}$ value of the test group to the $OD_{450\ nm}$ value of the control group is greater than 2.1, the sample is positive (Wang Zhaoyang et al., 2020); the results show that the reactivity of the four expressed nanobodies is still significantly higher than that of the negative control after dilution by 1,000 times, indicating that all four nanobodies can bind specifically to CPV. See Table 13 for the results of ELISA experiments.

TABLE 13

Experimental data of indirect ELISA

| Group | Antibody dilution multiple and $OD_{450nm}$ average value | | | | Judgment result |
|---|---|---|---|---|---|
| | 1:10 | 1:100 | 1:1,000 | 1:10,000 | |
| CPV-VHH-H1 | 2.56 | 2.46 | 0.28 | 0.10 | Positive (+) |
| CPV-VHH-E3 | 2.811 | 2.60 | 2.24 | 0.17 | Positive (+) |
| CPV-VHH-D4 | 2.87 | 2.64 | 2.29 | 0.27 | Positive (+) |
| CPV-VHH-F5 | 3.07 | 2.81 | 2.06 | 0.22 | Positive (+) |
| Negative control group | | | 0.07 | | |

3.4.2 Experimental Results of IFA

Figure 16:
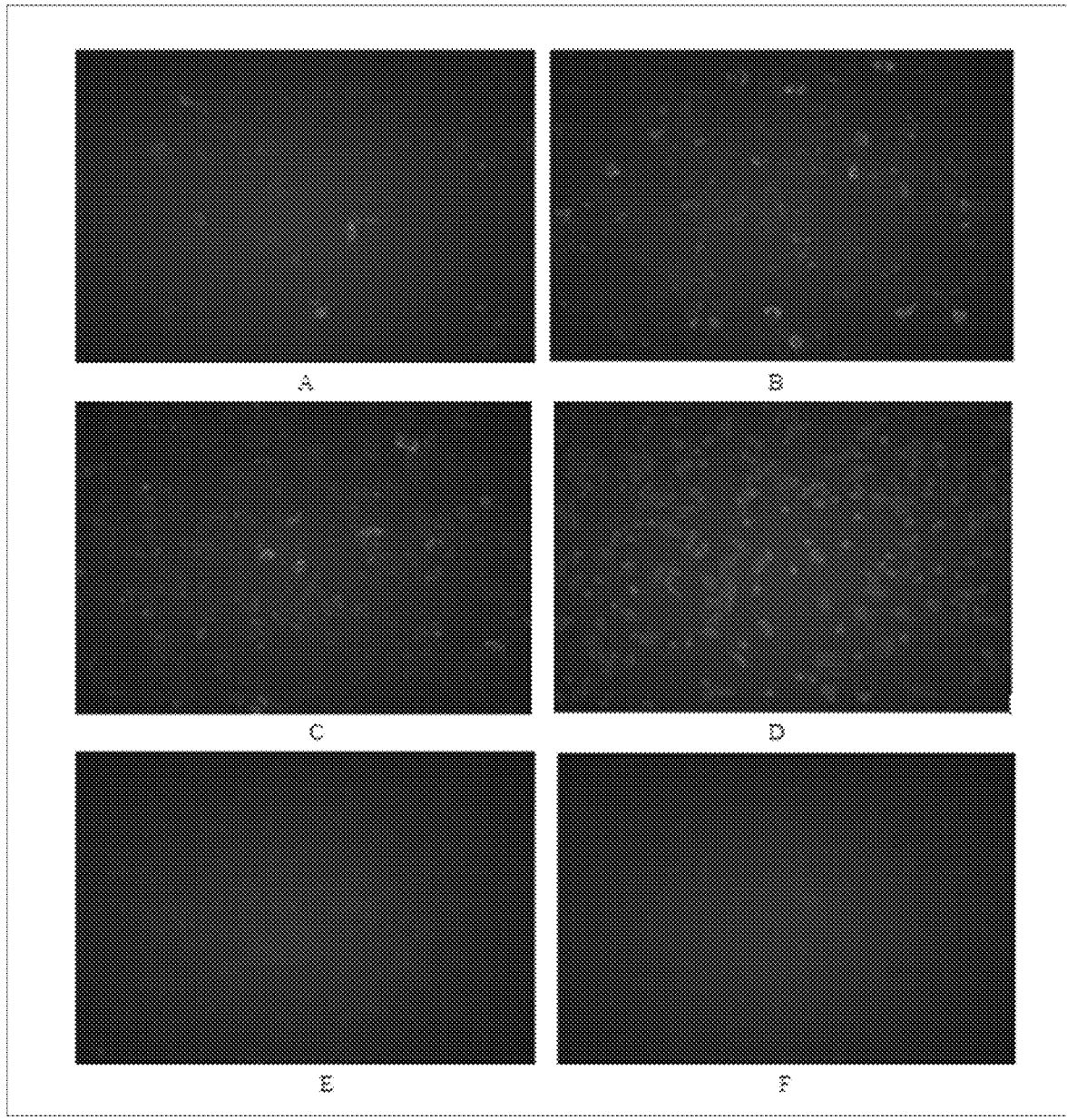
FIG. 16 shows the results of indirect immunofluorescence assay (IFA) test, where A: VHH CPV-H1; B: VHH CPV-E3; C: VHH CPV-D4; D: VHH CPV-F5; E: secondary antibody control group; and F: blank cell control group.

The specificity of four nanobodies to CPV is verified by IFA, as recombinant nanobodies carry 6×His tags, and if they can specifically bind CPV, the fluorescent signal can be seen using anti-His tag antibody with FITC tag as secondary antibody, and results show that all four recombinant nanobodies can bind specifically to CPV, see FIG. 16 for IFA results.

3.4.3 Results of Virus Neutralization Test

The neutralizing activity of the expressed recombinant nanobodies is detected by neutralization assay (VN) against CPV, results show that the neutralizing titer of all four nanobodies against CPV is less than 1:10, with a preliminary judgment of that the four VHHs do not possess CPV neutralizing activity, and the results of neutralizing antibody titer determination are shown in Table 14.

TABLE 14

Results of virus neutralization experiment

| Group | Antibody dilution multiple and CPE number | | Virus regression experiment | |
|---|---|---|---|---|
| | 1:10 | >1:10 | dilution | CPE number |
| CPV-VHH-H1 | 3/3 (+) | All (+) | 1(100 $TCID_{50}$) | 5/5(+) |
| CPV-VHH-E3 | 3/3 (+) | All (+) | $10^{-1}$(10 $TCID_{50}$) | 4/5(+) |
| CPV-VHH-D4 | 3/3 (+) | All (+) | $10^{-2}$(1 $TCID_{50}$) | 1/5(+) |
| CPV-VHH-F5 | 3/3 (+) | All (+) | $10^{-3}$(0.1 $TCID_{50}$) | 0/5(+) |
| Normal cell control | | | | 0/5(+) |
| Virus control | | | | 5/5(+) |

Note:
"+" means CPE appears in cell pores.

The present invention characterizes the biological properties of four recombinant nanobodies by SDS-PAGE, ELISA, IFA and neutralizing titer assay against CPV, with results showing that all four nanobodies expressed through HEK293F cells can specifically bind CPV, but do not possess neutralizing activity against CPV-2c strain. Possible reasons are as follows: (1) VHH screened by using whole virus in this experiment is not an antibody that recognizes key sites of virus-infected cells; the VP2 protein is an immunogenic protein of CPV, which contains neutralizing antigenic sites, and a more targeted and specific screening of phage library with CPV VP2 protein as the target antigen may be attempted, or nanobodies with neutralizing activity may be obtained (XU et al., 2014); (2) the molecular weight of the nanobodies is too small, which facilitates the binding of antigenic sites but is not sufficient to create an effective spatial site-blocking effect to block the ability of viruses from infecting cells; nanobodies can be modified by some genetic engineering means, such as constructing multimers or bispecific antibodies by tandemly linking nanobodies with flexible ligand peptides, therefore improving the function of nanobodies.

In addition, the expressed recombinant nanobodies have high CPV specificity and thus may be applied to CPV diagnostic studies, such as rapid diagnosis of diseases, antibody labeling, virus localization, etc.

The above-mentioned embodiments only describe the preferred mode of the present application, but do not limit the scope of the present application. On the premise of not departing from the design spirit of the present application, all kinds of modifications and improvements made by ordinary technicians in the field to the technical scheme of the present application shall fall within the scope of protection determined by the claims of the present application.

What is claimed is:

1. A canine parvovirus (CPV) nanobody CPV-VHH-E3, comprising a heavy chain variable region with an amino acid sequence as shown in SEQ ID NO: 1.

2. A gene encoding the CPV nanobody CPV-VPP-E3 of claim 1, comprising a nucleotide sequence as shown in SEQ ID NO: 2.

3. An expression vector containing the gene of claim 2.

4. The expression vector according to claim 3, wherein the expression vector comprises pcDNA3.1.

* * * * *